US012745963B2

(12) United States Patent
Nadig et al.

(10) Patent No.: US 12,745,963 B2
(45) Date of Patent: Sep. 29, 2026

(54) OPTICAL SIGNAL-QUALITY CONTROL WITH ACCELEROMETER-INDUCED SIGNALS

(71) Applicant: Google LLC, Mountain View, CA (US)

(72) Inventors: Sachin Prakash Nadig, San Francisco, CA (US); Chintan Trehan, Pleasanton, CA (US)

(73) Assignee: GOOGLE LLC, Mountain View, CA (US)

( * ) Notice: Subject to any disclaimer, the term of this patent is extended or adjusted under 35 U.S.C. 154(b) by 0 days.

(21) Appl. No.: 18/980,613

(22) Filed: Dec. 13, 2024

(65) Prior Publication Data

US 2026/0165658 A1 Jun. 18, 2026

(51) Int. Cl.
*A61B 5/00* (2006.01)
*A61B 5/024* (2006.01)

(52) U.S. Cl.
CPC .......... *A61B 5/721* (2013.01); *A61B 5/02416* (2013.01); *A61B 5/02438* (2013.01); *A61B 5/681* (2013.01); *A61B 5/7246* (2013.01); *A61B 5/7257* (2013.01); *A61B 5/7267* (2013.01); *A61B 5/742* (2013.01); *A61B 2562/0219* (2013.01)

(58) Field of Classification Search
CPC . A61B 5/721; A61B 5/02416; A61B 5/02438; A61B 5/681; A61B 5/7246; A61B 5/7257; A61B 5/7267; A61B 5/742; A61B 2562/0219
See application file for complete search history.

(56) References Cited

U.S. PATENT DOCUMENTS

| | | | | |
|---|---|---|---|---|
| 2003/0212336 A1* | 11/2003 | Lee | ...................... | A61B 5/7207 600/504 |
| 2018/0330810 A1* | 11/2018 | Gamarnik | .............. | G16H 10/20 |
| 2020/0138379 A1* | 5/2020 | Huiku | .................. | A61B 5/7221 |
| 2020/0337574 A1* | 10/2020 | Foroozan | ............ | A61B 5/7221 |

(Continued)

FOREIGN PATENT DOCUMENTS

| | | |
|---|---|---|
| CN | 117398075 | 1/2024 |
| WO | WO 2024114222 | 6/2024 |

OTHER PUBLICATIONS

Arpitha et al., "Deep Learning based Respiration Rate Estimation", 2023 Institute of Electrical and Electronics Engineers Women In Technology Conference, Bangalore, India, Sep. 21-21, 2023, pp. 1-6.

(Continued)

*Primary Examiner* — Kaitlyn E Sebastian
(74) *Attorney, Agent, or Firm* — DORITY & MANNING, P.A.

(57) ABSTRACT

A wearable computing device and system are provided. The wearable computing device includes a display device, an inertial measurement unit (IMU), an optical sensor(s), and a processor(s). The processor(s) is configured to obtain optical sensor data associated with a user of the wearable computing device, obtain movement data characterizing motion of the user, process the optical sensor data and the movement data to identify a motion-induced spurious component of the optical sensor data, and modify an operation mode of the wearable computing device based on the motion-induced spurious component of the optical sensor data.

18 Claims, 10 Drawing Sheets

(56) References Cited

U.S. PATENT DOCUMENTS

| | | | |
|---|---|---|---|
| 2020/0342996 | A1 | 10/2020 | Leboeuf et al. |
| 2021/0330207 | A1* | 10/2021 | Richards .............. A61B 5/7475 |
| 2022/0008019 | A1 | 1/2022 | Jones et al. |
| 2022/0313098 | A1 | 10/2022 | Leboeuf et al. |
| 2023/0033353 | A1* | 2/2023 | Cendrillon ......... A61B 5/02416 |
| 2023/0277075 | A1 | 9/2023 | Pantelopoulos et al. |

OTHER PUBLICATIONS

Extended European Search Report for Application No. EP 25222881.2, mailed Apr. 30, 2026, 16 pages.

* cited by examiner

OPTICAL SIGNAL-QUALITY CONTROL WITH ACCELEROMETER-INDUCED SIGNALS

FIELD

The present disclosure relates generally to wearable computing devices. More particularly, the present disclosure relates to wearable computing devices, as well as related systems and methods, for controlling and/or improving optical sensor signal accuracy.

BACKGROUND

Wearable biometric monitoring devices may be worn, for instance, on a user's wrist. Further, such wearable computing devices may also be operable to obtain sensor data from various biometric sensors and, as such, may be configured to determine various biometric parameters of the user. In certain instances, wearable computing devices may include one or more optical sensors, such as photoplethysmogram (PPG) sensors. More particularly, the optical sensor(s) may be configured to obtain and/or generate one or more optical signals indicative of a biometric parameter of the user. The optical sensor(s) may include one or more light emitters that each include one or more light sources (e.g., light-emitting diodes (LEDs)) configured to emit light toward a body part (e.g., wrist) of the user when the wearable computing device is worn by the user. The optical sensor(s) may further include one or more light detectors (e.g., photodiodes) configured to receive a reflection of the light emitted toward the body part (e.g., wrist) of the user from the light emitter(s).

SUMMARY

Aspects and advantages of embodiments of the present disclosure will be set forth in part in the following description, or can be learned from the description, or can be learned through practice of the embodiments.

In an aspect, the present disclosure is directed to a method. The method includes obtaining, via at least one optical sensor of a wearable computing device, optical sensor data associated with a user of the wearable computing device. The method further includes obtaining, via the wearable computing device, movement data characterizing a motion of the user. The method further includes processing, via the wearable computing device, the optical sensor data and the movement data to identify a motion-induced spurious component of the optical sensor data. The method further includes modifying, via the wearable computing device, an operation mode of the wearable computing device based on the motion-induced spurious component of the optical sensor data.

In some examples, processing the optical sensor data and the movement data to identify the motion-induced spurious component of the optical sensor data includes providing, via the wearable computing device, the optical sensor data and the movement data to a machine-learned model of the wearable computing device; determining, via the wearable computing device, a Fast Fourier Transform (FFT) for each of the optical sensor data and the movement data based on an output of the machine-learned model; and identifying, via the wearable computing device, the motion-induced spurious component of the optical sensor data based on a relationship between the FFT of the optical sensor data and the FFT of the movement data.

In some examples, the method further includes determining, via the wearable computing device, a biometric parameter associated with the user based on the optical sensor data and generating, via the wearable computing device, a notification for display to the user via a display device of the wearable computing device, the notification corresponding to the biometric parameter associated with the user.

In some examples, the biometric parameter is a heart rate (HR) of the user.

In some examples, generating the notification for display to the user includes, subsequent to determining the biometric parameter associated with the user, determining, via the wearable computing device, that the biometric parameter associated with the user is an erroneous biometric parameter based on the motion-induced spurious component of the optical sensor data and, in response to determining that the biometric parameter associated with the user is the erroneous biometric parameter, generating, via the wearable computing device, the notification for display to the user, the notification indicating that the biometric parameter is the erroneous biometric parameter.

In some examples, the method further includes, subsequent to determining that the biometric parameter associated with the user is the erroneous biometric parameter, determining, via the wearable computing device, a corrective action for the user based on the movement data and the motion-induced spurious component of the optical sensor data and providing, via the display device of the wearable computing device, a prompt to the user, the prompt corresponding to the corrective action, wherein the corrective action reduces a magnitude of the motion-induced spurious component of the optical sensor data.

In some examples, determining the biometric parameter associated with the user includes discarding, via the wearable computing device, the motion-induced spurious component of the optical sensor data; identifying, via the wearable computing device, a pulsatile component of the optical sensor data, the pulsatile component being different from the motion-induced spurious component; and determining, via the wearable computing device, the biometric parameter associated with the user based on the pulsatile component of the optical sensor data.

In some examples, modifying the operation mode of the wearable computing device includes determining, via the wearable computing device, an acceleration profile for the user based on the movement data, the acceleration profile characterizing a type of physical activity performed by the user and modifying, via the wearable computing device, the operation mode of the wearable computing device based on the type of physical activity characterized by the acceleration profile.

In some examples, the optical sensor of the wearable computing device comprises one or more light emitters and one or more light detectors. In some examples, obtaining the optical sensor data includes emitting, via the one or more light emitters of the optical sensor, one or more optical signals towards a body part of the user; receiving, via the one or more light detectors of the optical sensor, one or more reflected optical signals, the one or more reflected optical signals corresponding to the one or more optical signals emitted towards the body part of the user by the one or more light emitters; and generating, via the wearable computing device, the optical sensor data based on the one or more reflected optical signals received by the one or more light detectors of the optical sensor.

In some examples, modifying the operation mode of the wearable computing device comprises determining, via the wearable computing device, a current transfer ratio (CTR) for the user based on the optical sensor data; determining, via the wearable computing device, a target signal strength for the optical sensor based on the CTR; and configuring, via the wearable computing device, the one or more light emitters of the optical sensor to emit one or more adjusted optical signals, each of the one or more adjusted optical signals having the target signal strength.

In some examples, determining the CTR for the user includes, subsequent to processing the optical sensor data and the movement data to identify the motion-induced spurious component of the optical sensor data, determining, via the wearable computing device, a signal-to-noise ratio (SNR) for the optical sensor data based on the one or more reflected optical signals received by the one or more light detectors; determining, via the wearable computing device, a signal-to-motion ratio (SMR) for the optical sensor data based on the one or more reflected optical signals received by the one or more light detectors and the movement data; and determining, via the wearable computing device, the CTR for the user based on the SNR for the optical sensor data and the SMR for the optical sensor data.

In some examples, the method further includes determining, via the wearable computing device, an acceleration profile for the user based on the movement data, the acceleration profile characterizing a type of physical activity performed by the user; determining, via the wearable computing device, a correlation between the acceleration profile and the SMR for the optical sensor data; and storing, via the wearable computing device, the correlation in a memory of the wearable computing device.

In some examples, the SMR for the optical sensor data is a ratio between the one or more reflected optical signals received by the one or more light detectors of the optical sensor and the movement data at a particular frequency of the optical sensor data.

In some examples, the particular frequency corresponds to a frequency of the motion-induced spurious component of the optical sensor data.

In some examples, processing the optical sensor data and the movement data to identify the motion-induced spurious component of the optical sensor data includes providing, via the wearable computing device, the optical sensor data and the movement data to a machine-learned model of the wearable computing device; detecting, via the machine-learned model of the wearable computing device, a cadence event in the optical sensor data that is associated with the motion of the user; and, in response to detecting the cadence event in the optical sensor data, identifying, via the wearable computing device, the motion-induced spurious component of the optical sensor data.

In some examples, the method further includes providing, via the wearable computing device, data indicative of the cadence event to the machine-learned model as training data for the machine-learned model.

In another aspect, the present disclosure is directed to a wearable computing device. The wearable computing device includes a display device, an inertial measurement unit (IMU), one or more optical sensors, and one or more processors. The processor(s) are configured to obtain, via the one or more optical sensors, optical sensor data associated with a user of the wearable computing device. The processor(s) are further configured to obtain, via the IMU, movement data characterizing motion of the user. The processor(s) are further configured to process the optical sensor data and the movement data to identify a motion-induced spurious component of the optical sensor data. The processor(s) are further configured to modify an operation mode of the wearable computing device based on the motion-induced spurious component of the optical sensor data.

In some examples, to identify the motion-induced spurious component of the optical sensor data, the one or more processors are configured to provide the optical sensor data and the movement data to a machine-learned model of the wearable computing device, determine a Fast Fourier Transform (FFT) for each of the optical sensor data and the movement data based on an output of the machine-learned model, and identify the motion-induced spurious component of the optical sensor data based on a relationship between the FFT of the optical sensor data and the FFT of the movement data.

In some examples, the one or more processors are further configured to determine a biometric parameter associated with the user based on the optical sensor data and generate a notification for display to the user via the display device, the notification corresponding to the biometric parameter associated with the user. In some examples, the biometric parameter associated with the user is a heart rate (HR) of the user.

In another aspect, the present disclosure is directed to a computing system. The computing system includes an inertial measurement unit (IMU), one or more optical sensors, one or more processors, and one or more computer-readable media that collectively store instructions that, when executed by the one or more processors, cause the computing system to perform operations. The operations include obtaining, via the one or more optical sensors, optical sensor data associated with a user of the computing system. The operations further include obtaining, by the IMU, movement data characterizing motion of the user. The operations further include processing the optical sensor data and the movement data to identify a motion-induced spurious component of the optical sensor data. The operations further include modifying an operation mode of a wearable computing device of the computing system based on the motion-induced spurious component of the optical sensor data.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

Detailed discussion of embodiments directed to one of ordinary skill in the art are set forth in the specification, which makes reference to the appended figures, in which.

Figure 1:
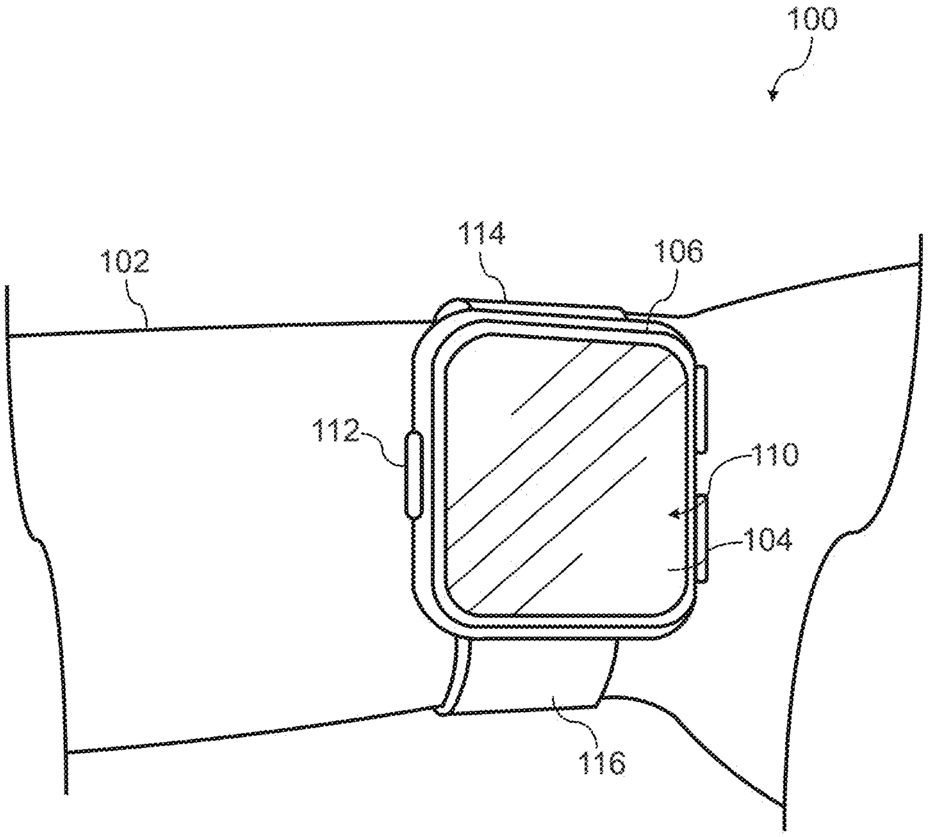
FIG. 1 depicts a perspective view of an example wearable computing device according to embodiments of the present disclosure.

Repeat use of reference characters in the present specification and drawings is intended to represent the same and/or analogous features or elements of the present invention.

DETAILED DESCRIPTION

Reference now will be made in detail to embodiments, one or more examples of which are illustrated in the drawings. Each example is provided by way of explanation of the embodiments, not limitation of the present disclosure. In fact, it will be apparent to those skilled in the art that various modifications and variations may be made to the embodiments without departing from the scope or spirit of the present disclosure. For instance, features illustrated or described as part of an embodiment may be used with another embodiment to yield a still further embodiment. Thus, it is intended that aspects of the present disclosure cover such modifications and variations.

Recent consumer interest in personal health has led to a variety of personal health monitoring devices being offered in the market. These personal health monitoring devices have gained popularity amongst consumers due to their ability to monitor and determine a variety of health-related information associated with a user of the device. For example, devices such as fitness trackers, smartwatches, and/or the like are able to monitor and determine information relating to the pulse or motion of the user of the device.

Moreover, recent advances in sensor, electronics, and power source miniaturization have allowed the size of personal health monitoring devices (also referred to herein as "biometric tracking" or "biometric monitoring" devices) to be offered in extremely small sizes that were previously impractical. For example, certain biometric monitoring devices may include a variety of sensors for measuring multiple biological parameters that can be beneficial to a user of the device, such as a heart rate sensor, multi-purpose electrical sensors compatible with electrocardiogram (ECG) and electrodermal activity (EDA) applications, red and infrared sensors, an inertial measurement unit (IMU), a gyroscope, an altimeter, an accelerometer, a temperature sensor, an ambient light sensor, Wi-Fi, GPS, a vibration or haptic feedback sensor, a speaker, and a microphone, among others. However, the amount and types of health-related information capable of being monitored and determined by such devices has conventionally been limited.

Some wearable biometric monitoring devices may be worn, for instance, on a user's wrist. Further, such wearable computing devices may also be operable to obtain sensor data from various biometric sensors and, as such, may be configured to determine various biometric parameters of the user. In certain instances, wearable computing devices may include one or more optical sensors, such as photoplethysmogram (PPG) sensors. More particularly, the optical sensor(s) may be configured to obtain and/or generate one or more optical signals indicative of a biometric parameter of the user. The optical sensor(s) may include one or more light emitters that each include one or more light sources (e.g., light-emitting diodes (LEDs)) configured to emit light toward a body part (e.g., wrist) of the user when the wearable computing device is worn by the user. The optical sensor(s) may further include one or more light detectors (e.g., photodiodes) configured to receive a reflection of the light emitted toward the body part (e.g., wrist) of the user from the light emitter(s).

However, in some instances, movement by the user—particularly during high-intensity activities (e.g., running, walking, etc.)—may result in erroneous optical signals received by the light detectors of the optical sensor. More particularly, the user's movement may result in spurious peaks in the frequency domain of the optical signal received by the light detectors of the optical sensor. These spurious peaks in the received optical signal may be the result of a cadence event, such as a cadence lock event and/or a cadence match event. As will be discussed in greater detail below, a "cadence event" refers to a situation where a user's rhythmic motion (e.g., cadence) interferes with the optical signals received by the light detector of the optical sensor (e.g., PPG sensor). That is, a user's cadence may cause spurious peaks in the frequency domain of the received optical signals, which are then misinterpreted by the wearable computing device as pulsatile signals and are subsequently used by the wearable computing device to determine a biometric parameter (e.g., heart rate (HR)) of the user. In such instances, the wearable computing device may generate erroneous biometric parameter determinations by making determining the corresponding biometric parameter for the user based on the spurious motion-induced component (e.g., spurious motion-induced peak) instead of the pulsatile component (e.g., pulsatile peak) of the received optical signal.

For instance, some wearable computing devices may choose a strong, motion-induced spurious component in the optical signal over a weaker (e.g., relative to the spurious motion-induced component) pulsatile component that, in actuality, corresponds to a physiological signal of the user. In such instances, the resulting biometric parameter of the user—e.g., as determined by the wearable computing device—may be erroneous. As an example, strong spurious motion-induced component in the received optical signals may cause a corresponding HR determination to have errors on the order of about 10 beats-per-minute (BPM) to about 40 beats-per-minute (BPM) or more.

To address the aforementioned issues, some wearable computing devices employ a motion compensation algorithm to attenuate these spurious motion-induced components in the received optical signal(s), thereby allowing the pulsatile component in the optical signal(s) to be used for biometric parameter determination by the wearable computing device. However, a number of issues (e.g., band attachment on the user's wrist, motion variations, wrist-size variations, etc.) cause the pulsatile component of the optical signal received at the light detector to be too weak for accurate biometric parameter determinations of the user.

Accordingly, example aspects of the present disclosure are directed to wearable computing devices, as well as related systems and methods, that control and/or improve the accuracy of the optical signals received by the optical sensor (such as a PPG sensor) and, hence, the biometric parameter determinations that are made based on the received optical signals by leveraging movement data (e.g., generated by accelerometer of the wearable computing device) associated with the user. More particularly, as described herein, the wearable computing device of the present disclosure may obtain optical sensor data (e.g., via an optical sensor) associated with a user of the wearable computing device. The wearable computing device may further obtain movement data (e.g., via an inertial measurement unit (IMU), an accelerometer, etc.) that characterizes a motion of the user. The wearable computing device may process the optical sensor data and the movement data (e.g., via a machine-learned model) to identify a motion-induced spurious component in the optical sensor data.

For instance, in some examples, the wearable computing device may provide the optical sensor data and the movement data to the machine-learned model of the wearable computing device. In such examples, the machine-learned model may detect a cadence event in the optical sensor data that is associated with the motion of the user, and, in response, the wearable computing device may identify the motion-induced spurious component of the optical sensor data. Furthermore, in some examples, data indicative of the cadence event may be provided to the machine-learned model as training data for the machine-learned model.

More particularly, as described in greater detail below, the wearable computing device may include a machine-learned model that is configured to receive data, such as the optical sensor data and the movement data, as an input. In some examples, the wearable computing device may be operable to determine a Fast Fourier Transform (FFT) for each of the optical sensor data and the movement data (e.g., inputs to the machine-learned model) based on an output of the machine-learned model. In such examples, the wearable computing device may identify the motion-induced spurious component of the optical sensor data based on a relationship between the FFT of the optical sensor data and the FFT of the movement data.

In some examples, the wearable computing device may modify an operation mode of the wearable computing device based on the motion-induced spurious component of the optical sensor data. More particularly, as will be discussed in greater detail below, the "operation mode" of the wearable computing device may, in some examples, correspond to a current transfer ratio (CTR) of the alternating current (AC) signal provided by light emitter(s) of the optical sensor. For instance, in some examples, light emitter(s) of the optical sensor may emit optical signal(s) towards a body part (e.g., wrist) of the user, and light detector(s) of the optical sensor may receive one or more reflected optical signals that correspond to the optical signal(s) emitted towards the body part of the user by the light emitter(s). The wearable computing device may further generate the optical sensor data based on the reflected optical signal(s) received by the light detector(s) of the optical sensor.

Subsequent to generating the optical sensor data, the wearable computing device may determine the CTR for the user based on the optical sensor data. Based on the determined CTR, the wearable computing device may determine a target signal strength for the optical sensor. The wearable computing device may then configure the light emitter(s) of the optical sensor to emit one or more adjusted optical signals—each of which having the target signal strength—which results in an increase of the signal strength of the pulsatile component(s) of the optical signal(s) received by the light detector(s) of the optical sensor. As such, the wearable computing device may determine one or more biometric parameters for the user, such as HR, based on pulsatile signals (e.g., pulsatile component(s)) of the optical signal(s) received by the light detector(s) instead of the motion-induced spurious component(s), thereby reducing motion-induced errors in the biometric parameter determinations made by the wearable computing device.

In some examples, to determine the CTR for the user, the wearable computing device may determine a signal-to-noise ratio (SNR) for the optical sensor data based on the reflected optical signal(s) received by the light detector(s) of the optical sensor. Furthermore, in some examples, the wearable computing device may also determine a signal-to-motion ratio (SMR) for the optical sensor data based on the reflected optical signal(s) and the movement data. In such examples, the wearable computing device may determine the CTR for the user based on the SNR for the optical sensor data and the SMR for the optical sensor data. It should be understood that, as used herein, the "signal-to-motion ratio (SMR)" for optical sensor data refers to a ratio between the reflected optical signal(s) received by the light detector(s) of the optical sensor and the movement data at a particular frequency (e.g., corresponding to a frequency of the motion-induced spurious component) of the optical sensor data.

In some examples, the wearable computing device may determine an acceleration profile for the user based on the movement data. As discussed in greater detail below, an "acceleration profile" may characterize a type of physical activity being performed by the user. The wearable computing device may determine a correlation between the acceleration profile and the SMR for the optical sensor data and may store the correlation in a memory of the wearable computing device. By storing the correlation in the memory of the wearable computing device, the wearable computing device may be operable to make future operation-mode determinations based on the type of physical activity being performed by the user, thereby minimizing processing times, required computational resources, and/or the like.

It should be understood that, as used herein, a "pulsatile component," a "pulsatile signal," and/or a "pulsatile peak" refers to one or more components of the optical signal(s) received by the optical sensor that correspond to changes in arterial blood volume caused by the user's heartbeat. Conversely, as used herein, a motion-induced "spurious component," "spurious signal," and/or "spurious peak" refers to one or more components of the optical signal(s) received by the optical sensor that correspond to motion-induced changes caused by the user's motion.

In some examples, the wearable computing device of the present disclosure may determine a biometric parameter associated with the user based on the optical sensor data and may subsequently generate a notification for display to the user (e.g., via the display device of the wearable computing device) that corresponds to the determined biometric parameter of the user. In some examples, subsequent to determining the biometric parameter associated with the user, the wearable computing device may determine that the biometric parameter associated with the user is an erroneous biometric parameter based on the motion-induced spurious component of the optical sensor data. In such examples, the wearable computing device may generate a notification for display to the user (e.g., via the display device of the wearable computing device) that indicates the determined biometric parameter is erroneous. By way of a non-limiting example, the wearable computing device may generate a haptic notification, an auditory notification, a visual notification, and/or the like. It should be understood that the notification may be any suitable notification without deviating from the scope of the present disclosure.

In some examples, subsequent to determining that the biometric parameter associated with the user is the erroneous biometric parameter, the wearable computing device may determine a corrective action for the user based on the movement data and the motion-induced spurious component of the optical sensor data. The wearable computing device may also provide a prompt to the user (e.g., via the display device of the wearable computing device) that corresponds to the corrective action. As described in greater detail below, the corrective action may be an action that reduces a magnitude of the motion-induced spurious component of the optical sensor data, such as, by way of non-limiting example, an adjustment to how and/or where the user is wearing the wearable computing device, an adjustment to a strap and/or band attachment that secures the wearable computing device to the user, and/or the like.

Example aspects of the present disclosure provide numerous technical effects and benefits. As an example, the systems and methods of the present disclosure provide improved techniques for obtaining and determining biometric information associated with a user. For instance, example aspects of the present disclosure provide for increased accuracy of optical sensor data obtained by the wearable computing device by processing the obtained optical sensor data with movement data that characterizes motion of the user. In this manner, example wearable computing devices of the present disclosure may identify a motion-induced spurious component of the optical sensor data based on the movement data. By identifying a motion-induced spurious component of the optical sensor data, wearable computing devices of the present disclosure may decrease motion-related biometric calculation errors and, hence, may accurately compensate for the motion of the user. In addition, example aspects of the present disclosure may determine and/or modify an operation mode of the wearable computing device based on the motion-induced spurious component of the optical sensor data. For instance, a wearable computing device of the present disclosure may configure a signal strength of an optical signal emitted by the light emitter(s) of the optical sensor based on the motion-induced spurious component(s) identified in the optical sensor data, which may reduce the magnitude, quantity, etc. of motion-induced spurious component(s). In this way, wearable computing devices of the present disclosure may be dynamically configured to increase the accuracy of biometric parameter determination, diagnoses, user health-related outcomes, and/or the like. As such, the disclosed system may significantly reduce the cost and time needed to provide diagnostic information and may result in improved medical care for users.

Furthermore, the systems and methods described herein may provide resulting improvements to computing technology tasked with monitoring and detecting biometric parameters in users. Improvements in the speed and accuracy of determining and detecting user biometric parameters can directly improve operational speeds for computing systems. For instance, by improving diagnostic accuracy (e.g., by reducing erroneous biometric determinations caused by motion-induced spurious peaks), the number of duplicative diagnostic operations can be reduced—thereby reducing processing and storage requirements for the computing systems. Hence, the reduced processing and storage requirements ultimately result in more efficient resource use for the computing system. In this way, valuable computing resources within a computing system that would have otherwise been needed for such tasks may be reserved for other tasks (e.g., extracting and processing additional cardiac information from biometric data, increasing storage capacity, etc.).

As used herein, the terms “first,” “second,” and “third” may be used interchangeably to distinguish one component from another and are not intended to signify location or importance of the individual components. The terms “includes” and “including” are intended to be inclusive in a manner similar to the term “comprising.” Similarly, the term “or” is generally intended to be inclusive (e.g., “A or B” is intended to mean “A or B or both”). The term “at least one of” in the context of, e.g., “at least one of A, B, and C” refers to only A, only B, only C, or any combination of A, B, and C. In addition, here and throughout the specification and claims, range limitations may be combined and/or interchanged. Such ranges are identified and include all the sub-ranges contained therein unless context or language indicates otherwise. For example, all ranges disclosed herein are inclusive of the endpoints, and the endpoints are independently combinable with each other. The singular forms “a,” “an,” and “the” include plural references unless the context clearly dictates otherwise.

Approximating language, as used herein throughout the specification and claims, may be applied to modify any quantitative representation that could permissibly vary without resulting in a change in the basic function to which it is related. Accordingly, a value modified by a term or terms, such as “generally,” “about,” “approximately,” and “substantially,” are not to be limited to the precise value specified. In at least some instances, the approximating language may correspond to the precision of an instrument for measuring the value, or the precision of the methods or machines for constructing or manufacturing the components and/or systems. For example, the approximating language may refer to being within a 10 percent margin, i.e., including values within ten percent greater or less than the stated value. In this regard, for example, when used in the context of an angle or direction, such terms include within ten degrees greater or less than the stated angle or direction, e.g., “generally vertical” includes forming an angle of up to ten degrees in any direction, e.g., clockwise or counterclockwise, with the vertical direction V.

The word “exemplary” is used herein to mean “serving as an example, instance, or illustration.” In addition, references to “an embodiment” or “an embodiment” do not necessarily refer to the same embodiment, although it may. Any implementation described herein as “exemplary” or “an embodiment” is not necessarily to be construed as preferred or advantageous over other implementations. Moreover, each example is provided by way of explanation of the invention, not limitation of the invention. In fact, it will be apparent to those skilled in the art that various modifications and variations can be made in the present invention without departing from the scope of the invention. For instance, features illustrated or described as part of an embodiment can be used with another embodiment to yield a still further embodiment. Thus, it is intended that the present invention covers such modifications and variations as come within the scope of the appended claims and their equivalents.

Relative terms such as “below” or “above” or “upper” or “lower” or “horizontal” or “lateral” or “vertical” may be used herein to describe a relationship of one element, layer or region to another element, layer or region as illustrated in the figures. It will be understood that these terms are intended to encompass different orientations of the device in addition to the orientation depicted in the figures. Furthermore, unless otherwise defined, all terms (including technical and scientific terms) used herein have the same meaning as commonly understood by one of ordinary skill in the art to which this invention belongs. It will be further understood that terms used herein should be interpreted as having a meaning that is consistent with their meaning in the context of this specification and the relevant art and will not be interpreted in an idealized or overly formal sense unless expressly so defined herein.

In the drawings and specification, there have been disclosed typical embodiments and, although specific terms are employed, they are used in a generic and descriptive sense only and not for purposes of limitation of the scope set forth in the following claims. Furthermore, like numbers refer to like elements throughout. Thus, the same or similar numbers may be described with reference to other drawings even if they are neither mentioned nor described in the corresponding drawing. Also, elements that are not denoted by reference numbers may be described with reference to other drawings.

Figure 2:
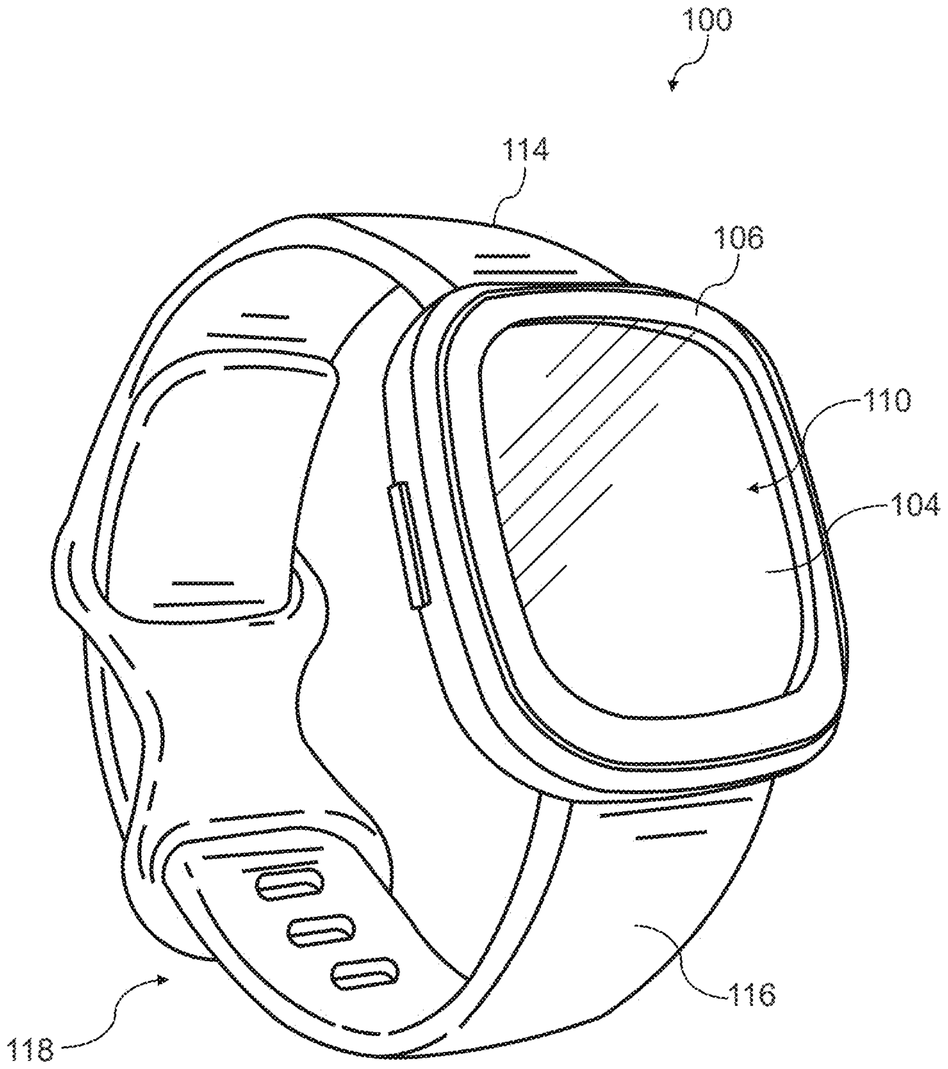
FIG. 2 depicts a front perspective view of the example wearable computing device of FIG. 1 according to embodiments of the present disclosure.
Figure 3:
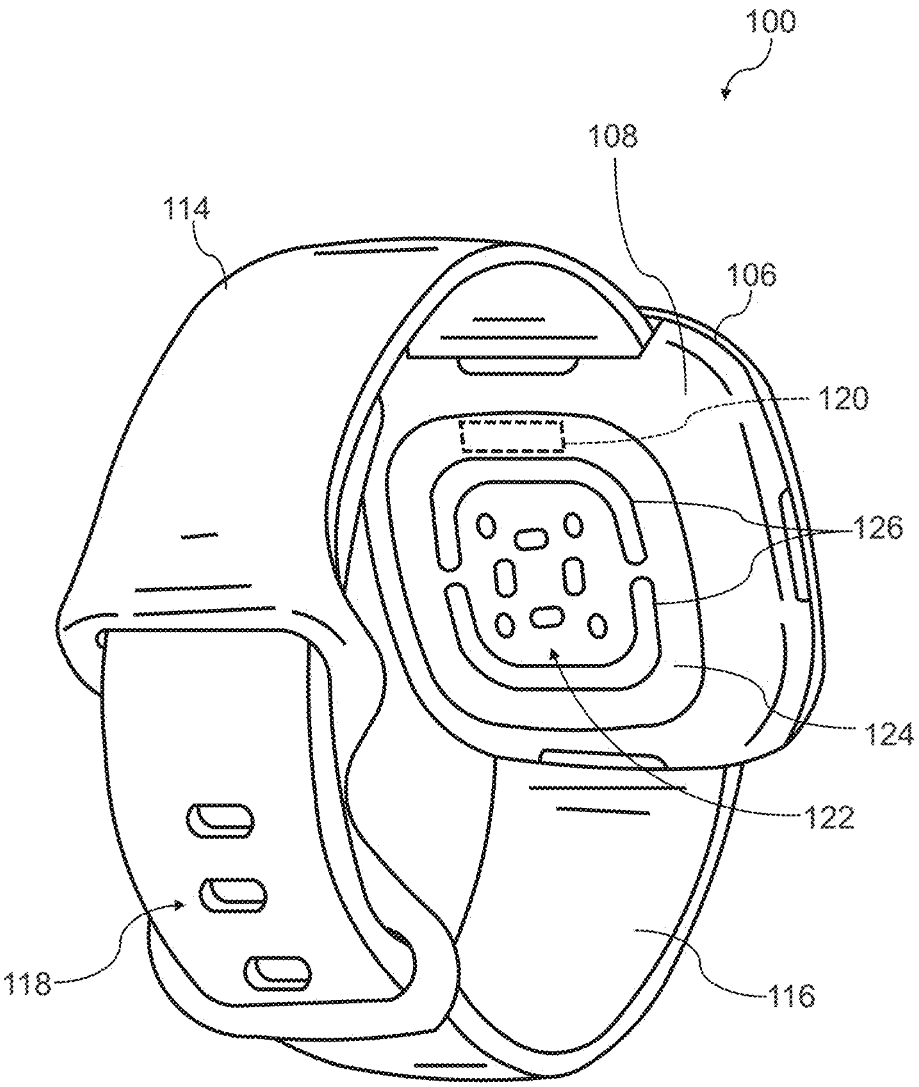
FIG. 3 depicts a rear perspective view of the example wearable computing device of FIG. 1 according to embodiments of the present disclosure.

Referring now to FIGS. 1-3, an example wearable computing device 100 is depicted according to example embodiments of the present disclosure. In particular, FIG. 1 depicts a perspective view of a user 102 wearing the wearable computing device 100, FIG. 2 depicts a front perspective view of the wearable computing device 100, and FIG. 3 depicts a rear perspective view of the wearable computing device 100. It should be understood that example aspects of the present disclosure are discussed with reference to the wearable computing device 100 for purposes of illustration and discussion, and those having ordinary skill in the art, using the disclosures provided herein, will understand that example aspects of the present disclosure may be implemented with any suitable computing device without deviating from the scope of the present disclosure.

As shown, the wearable computing device 100 may be worn on a distal location of the user 102, such as, by way of non-limiting example, an arm (e.g., wrist) of the user 102. In some examples, although not depicted in FIGS. 1-3, the wearable computing device 100 may be worn on another distal location of the user 102 (e.g., ankle, foot, etc.) and/or on a proximal location of the user 102 (e.g., inner side of knee, inner side of elbow, etc.). Those having ordinary skill in the art, using the disclosures provided herein, will understand that the wearable computing device 100 may be any suitable wearable computing device, such as, by way of non-limiting example, a ring, band, earring, necklace, and/or the like.

The wearable computing device 100 may include an outer covering 104 and a housing 106 that contains the electronics associated with the wearable computing device 100. In some examples, the outer covering 104 may include glass, polycarbonate, acrylic, and/or the like. The housing 106 may include a base plate 108 coupled to the housing 106. In this manner, the base plate 108 may define a bottom surface of the housing 106. The housing 106 may define a cavity (e.g., internal volume) (not shown) in which one or more electronic components (e.g., disposed on printed circuit boards) are disposed. For instance, the wearable computing device 100 may include a printed circuit board (e.g., flexible printed circuit board) (not shown) disposed within the cavity. Furthermore, one or more electronic components may be disposed on the printed circuit board. The wearable computing device 100 may further include a battery (not shown) that is disposed within the cavity defined by the housing 106.

As shown, the wearable computing device 100 may further include a display device 110 arranged within the housing 106 and viewable through the outer covering 104. That is, in some examples, the outer covering 104 may be positioned on the housing 106 such that the outer covering 104 is positioned above (e.g., on top of) the display device 110. In this manner, the outer covering 104 may be configured as a display cover for the display device 110 and, hence, may protect the display device 110 from being damaged (e.g., scratched, cracked, etc.). In some examples, the display device 110 may cover an electronics package (not shown), which may also be housed within the housing 106. In some examples, the wearable computing device 100 may include a seal (not shown) positioned between the housing 106 and the outer covering 104. For instance, in some examples, a first surface of the seal (now shown) may contact the housing 106 and a second surface of the seal (not shown) may contact the outer covering 104. In this manner, the seal between the housing 106 and the outer covering 104 may prevent a liquid (e.g., water) from entering the cavity defined by the housing 106.

The display device 110 may be configured to display content (e.g., time, date, biometrics, notifications, etc.) for viewing by the user 102. The display device 110 may include a plurality of pixels (not shown). For instance, in some examples, the display device 110 may include an organic light-emitting diode (OLED) display. Those having ordinary skill in the art, using the disclosures provided herein, will understand that the display device 110 may include any suitable type of display device without deviating from the scope of the present disclosure.

The wearable computing device 100 may further include one or more buttons 112. The button(s) 112 may be implemented to provide a mechanism to activate various sensors of the wearable computing device 100 to collect certain health-related data associated with the user 102.

As shown, in some examples, the wearable computing device 100 may be worn on a forearm and/or wrist of the user 102 like a wristwatch. That is, the wearable computing device 100 may include a first band 114 coupled to the housing 106 (e.g., at a first location) and a second band 116 coupled to the housing 106 (e.g., at a second location). The first band 114 and the second band 116 may be coupled to one another (e.g., at a third location) (not shown) to secure the housing 106 to the arm of the user 102. For instance, the first band 114 may include a buckle, clasp, and/or the like (not shown). Additionally, the second band 116 may include a plurality of openings 118 spaced apart from one another along a length of the second band 116. In some examples, a prong of the buckle, clasp, etc. associated with the first band 114 may extend through one of a plurality of openings 118 defined by the second band 116 to couple the first band 114 to the second band 116.

It should be understood that the first band 114 may be coupled to the second band 116 using any suitable type of fastener. For instance, in some examples, the first band 114 and the second band 116 may include a magnet (not shown). In such examples, the first band 114 and the second band 116 may be magnetically coupled to one another to secure the housing 106 to the arm of the user 102.

As described herein, the wearable computing device 100 may include a variety of sensors within the housing 106. More particularly, the wearable computing device 100 may include one or more motion sensors 120 operable to obtain movement data associated with the user 102. That is, the motion sensor(s) 120 may obtain movement data characterizing motion of the user 102. The motion sensor(s) 120 may include any suitable motion sensor, such as, by way of non-limiting example, inertial measurement unit(s) (IMU(s)), gyroscope(s), accelerometer(s), altimeter(s), and/ or the like. For instance, the motion sensor(s) 120 may include one or more accelerometer(s) for sensing an acceleration, velocity, etc. of the wearable computing device 100 in each of, for instance, three orthogonal directions (x, y, z). Additionally and/or alternatively, in some examples, the motion sensor(s) 120 may include one or more gyroscopes for sensing a rotation of the wearable computing device 100 about each of, for example, three orthogonal axes.

Referring particularly to FIG. 3, the wearable computing device 100 may further include an optical sensor package 122 for measuring and/or obtaining optical sensor data indicative of one or more biometric parameters associated with the user 102 of the wearable computing device 100. More particularly, as shown in FIG. 3, the wearable computing device 100 may include a dorsal wrist-side face 124 configured to contact a dorsal wrist of the user 102 when the wearable computing device 100 is worn by the user 102. The optical sensor package 122 may be disposed on and/or in the dorsal wrist-side face 124 of the wearable computing device 100 so as to maintain skin contact with the user 102 when the wearable computing device 100 is being worn by the user 102.

The optical sensor package 122 (hereinafter "optical sensor(s) 122") may include any suitable optical sensor, such as one or more photoplethysmogram (PPG) sensors configured to obtain optical PPG measurements. As described in greater detail below, the optical sensor(s) 122 may include one or more light emitters and one or more light detectors. The optical sensor(s) 122 may further include a lens extending across the optical sensor(s) 122 such that light signals emitted from the light emitter(s) may exit the housing 106 of the wearable computing device 100 via the lens. In this way, the light emitter(s) and light detector(s) of the optical sensor(s) 122 may be disposed such that the lens may also cover and/or protect the light emitter(s) and light detector(s) of the optical sensor(s) 122.

In some examples, the wearable computing device 100 may further include one or more sensor electrodes 126, such as one or more electrocardiogram (ECG) sensors. In some examples, such as that depicted in FIG. 3, the sensor electrode(s) 126 may be disposed around the optical sensor(s) 122 on the dorsal wrist-side face 124 of the wearable computing device 100 so as to maintain skin contact with the user 102 when the wearable computing device 100 is being worn by the user 102. More particularly, the sensor electrode(s) 126 may be positioned within respective apertures (e.g., cutouts) defined by the housing 106. It should be understood that, although depicted as having two sensor electrodes 126, the wearable computing device 100 may include more, or fewer, sensor electrode(s) 126 without deviating from the scope of the present disclosure. As described herein, each of the sensor electrode(s) 126 may be configured to measure and/or obtain electrical impedance data of the user 102 at a location of the skin contact on the wrist of the user 102. That is, the sensor electrode(s) 126 may be operable to measure one or more biometric parameters (e.g., electrodermal activity, electrocardiogram, body impedance, skin temperature, etc.) of the user 102.

Although not depicted in FIGS. 1-3, the wearable computing device 100 may further include one or more additional sensors within the cavity defined by the housing 106. For instance, in some examples, the wearable computing device 100 may include one or more temperature sensors (e.g., ambient temperature sensor, skin temperature sensor, etc.), one or more humidity sensors, one or more light sensors, one or more pressure sensors, one or more microphones, and/or the like.

Figure 4:
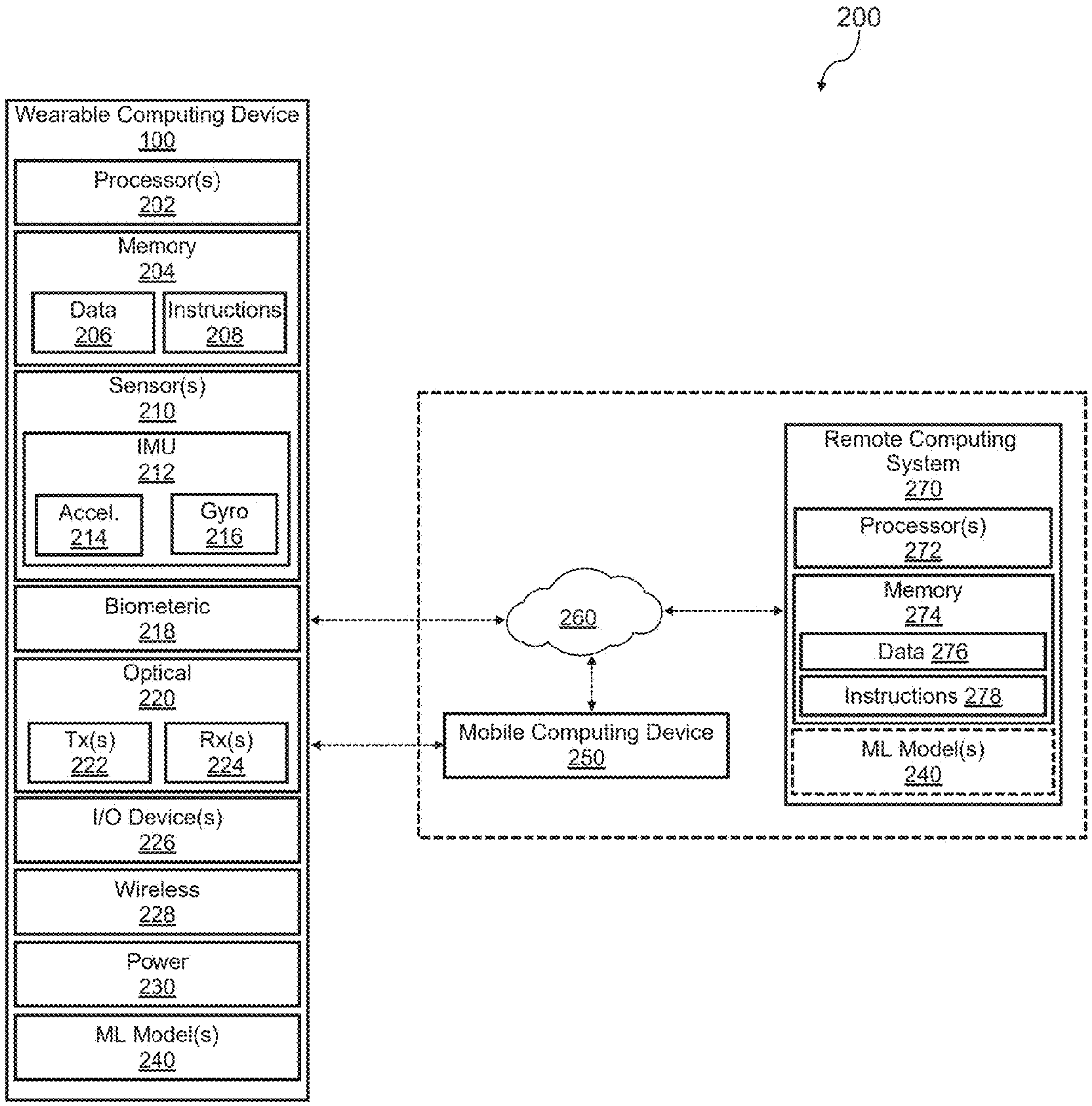
FIG. 4 depicts a block diagram of an example computing system according to embodiments of the present disclosure.

FIG. 4 depicts a block diagram of an example computing system 200 according to example embodiments of the present disclosure. Furthermore, a block diagram of various components of the example wearable computing device 100 discussed above with reference to FIGS. 1-3 are depicted according to example embodiments of the present disclosure. It should be understood that aspects of the present disclosure may be implemented by the wearable computing device 100 in isolation and/or across various components of the example computing system 200 without deviating from the scope of the present disclosure.

As shown, the wearable computing device 100 may include one or more processors 202. The processor(s) 202 may include any suitable processing device (e.g., a processor core, a microprocessor, an application specific integrated circuit (ASIC), a field programmable gate array (FPGA), a microcontroller, etc.). The wearable computing device 100 may further include a memory 204. The memory 204 may include one or more non-transitory computer-readable storage media, such as random access memory (RAM), read-only memory (ROM), electronically erasable programmable ready-only memory (EEPROM), erasable programmable read-only memory (EPROM), flash memory devices, and combinations thereof. The memory 204 may store data 206 and instructions 208 that, when executed by the processor(s) 202, cause the processor(s) 202 to perform operations, such as any of the operations described herein.

The wearable computing device 100 may include a plurality of sensors 210. For instance, in some examples, the plurality of sensors 210 may include an inertial measurement unit (IMU) 212, such as a steady IMU. In some examples, the IMU 212 may include one or more sensors, such as one or more accelerometers 214 (e.g., multi-axis accelerometer), one or more gyroscopes 216, and/or the like. In this manner, the IMU 212 may obtain movement data (e.g., acceleration, angular velocity, etc.) indicative of movement of the user. The plurality of sensors 210 may further include sensors and/or devices operable to determine a position and/or location of the user, such as, for instance, a navigational positioning system (not shown). In some examples, the navigational positioning system may include a global positioning system (GPS) (not shown), a compass (not shown), and the like. The navigational positioning system may be operable to generate location data corresponding to a physical location of the user.

In some examples, the plurality of sensors 210 may include one or more biometric sensors 218. For instance, the biometric sensor(s) 218 may be positioned on the bottom surface of the housing 106 (FIGS. 1-3) of the wearable computing device 100. In this manner, the biometric sensor(s) 218 may obtain biometric data of the user wearing the wearable computing device 100. For instance, in some examples, the biometric sensor(s) 218 may include a temperature sensor configured to measure and/or obtain temperature data associated with the user of the wearable computing device 100, such as, by way of non-limiting example, skin temperature data indicative of a skin temperature of the user, tissue temperature data indicative of a temperature of subcutaneous tissue of the user, muscle temperature data indicative of a temperature of muscle tissue of the user, and core temperature data indicative of a core temperature of the user. Additionally and/or alternatively, in some embodiments, the biometric sensor(s) 218 may include an impedance sensor (e.g., sensor electrode(s) 126) configured to measure a body impedance of the user wearing the wearable computing device 100. It should be understood that the one or more biometric sensor(s) 218 may include any suitable biometric sensor configured to obtain biometric data of the user wearing the wearable computing device 100 without deviating from the scope of the present disclosure.

In some examples, the plurality of sensors 210 may further include one or more optical sensors 220, such as one or more photoplethysmogram (PPG) sensors. As described above, the optical sensor(s) 220 may include one or more light emitters 222 and one or more light detectors 224 for measuring and/or obtaining optical sensor data indicative of one or more biometric parameters associated with the user. In some examples, the light emitter(s) 222 and the light detector(s) 224 of the optical sensor(s) 220 may be coupled to the processor(s) 202. For instance, in some examples, the light emitter(s) 222 and the light detector(s) 224 of the optical sensor(s) 220 may be directly coupled and/or indirectly coupled to the processor(s) 202 using driver circuitry (not shown). In this manner, the processor(s) 202 may be operable to drive the light emitter(s) 222 and obtain optical signals from the light detector(s) 224.

More particularly, in some examples, the light emitter(s) 222 may emit one or more optical signals towards a body part of the user, such as a dorsal wrist of the user, and the light detector(s) 224 may receive one or more reflected optical signals. As described above, the reflected optical signal(s) received by the light detector(s) 224 may correspond to the optical signal(s) emitted towards the body part of the user by the light emitter(s) 222. In this manner, the wearable computing device 100 may be operable to generate the optical sensor data based on the reflected optical signal(s) received by the light detector(s) 224 of the optical sensor(s) 220. As described in greater detail below, the wearable computing device 100 may be further configured to determine a biometric parameter (e.g., physiological metric) associated with the user based on the optical sensor data, such as, by way of non-limiting example, a heart rate (HR) of the user and/or the like.

In some examples, the optical sensor(s) 220 may include a single light emitter 222 and a single light detector 224 (e.g., a single light path). Additionally and/or alternatively, in some examples, the optical sensor(s) 220 may employ multiple light sources coupled to a single light detector 224 and/or multiple light detectors 224 (e.g., two or more light paths). Additionally and/or alternatively, in some examples, the optical sensor(s) 220 may employ multiple light detectors 224 coupled to a single light source and/or multiple light sources (e.g., two or more light paths).

The light emitter(s) 222 may be configured to emit a light signal having any suitable wavelength, such as one or more of green light, red light, infrared (IR) light, and/or the like. In some examples, the optical sensor(s) 220 may include a single light emitter 222 and two or more light detectors 224 that are each configured to detect a specific wavelength or wavelength range. For instance, each light detector 224 may, in some examples, be configured to detect a different and/or distinct wavelength and/or wavelength range relative to one another. Additionally and/or alternatively, in other examples, each light detector 224 may be configured to detect the same wavelength and/or wavelength range relative to one another. In examples employing multiple light paths, the optical sensor(s) 220 may determine an average of the reflected optical signals resulting from the multiple light paths before determining the biometric parameter associated with the user.

It should be understood that the optical sensor(s) 220 of the wearable computing device 100 are described herein as PPG sensor(s) for purposes of illustration and discussion. Those having ordinary skill in the art, using the disclosures provided herein, will understand that the optical sensor(s) 220 may be any suitable optical sensor have any number of light emitter(s) and/or light detector(s) without deviating from the scope of the present disclosure.

In some examples, the wearable computing device 100 may include one or more output devices 226. For instance, in some examples, the output device(s) 226 may include a display device, such as a display screen (e.g., display device 110). In this manner, the wearable computing device 100 may display content (e.g., time, date, biometrics, notifications, etc.) that can be viewed by the user. Additionally and/or alternatively, in some examples, the output device(s) 226 may include one or more speakers. In this manner, the wearable computing device 100 may emit audible noises (e.g., alarms, voice automated messages, etc.) for the user. Additionally and/or alternatively, in some examples, the output device(s) 226 may include one or more haptic devices operable to generate haptic notifications for the user, such as vibratory notifications and/or the like.

In some examples, the plurality of sensors 210 may be communicatively coupled to the processor(s) 202. More particularly, the processor(s) 202 may be communicatively coupled to the plurality of sensors 210 via a data interface (e.g., data bus). In this manner, the processor(s) 202 may obtain data from the plurality of sensors 210.

In some examples, sensor data obtained from the plurality of sensors 210 of the wearable computing device 100 may indicate whether the wearable computing device 100 is currently being worn by the user. For instance, in some examples, the biometric data obtained from the biometric sensor(s) 218 and/or optical sensor data obtained by the optical sensor(s) 220 may indicate the wearable computing device 100 is not being worn (e.g., off-wrist) by the user. In such examples, the processor(s) 202 may be configured to disable data collection functionality while the sensor data obtained from the plurality of sensors 210 indicates the wearable computing device 100 is not being worn by the user. In this manner, erroneous data from the plurality of sensors 210 may be ignored. It should be understood that the processor(s) 202 may be configured to enable data collection functionality when the sensor data obtained from the plurality of sensors 210 indicates the wearable computing device 100 is being worn (e.g., on-wrist) by the user.

The wearable computing device 100 may further include one or more wireless components 228 operable to communicate with one or more electronic devices within a communication range of the particular wireless channel. The wireless channel may be any suitable channel used to enable wireless communication between devices, such as, by way of non-limiting example, Bluetooth®, cellular, near-field communication (NFC), ultra-wideband (UWB), Wi-Fi, and/or the like. It should be understood that the wearable computing device 100 may further include one or more conventional wireless communication connections. The wearable computing device 100 may further include one or more power components 230, such as a battery operable to be recharged through conventional plug-in approaches and/or other approaches (e.g., capacitive charging through proximity with a power mat or other such device).

The wearable computing device 100 may further include one or more machine-learned (ML) models 240. In some examples, the machine-learned model(s) 240 may be stored in the memory 204. In other examples, as described in greater detail below, the machine-learned model(s) 240 may be stored in the memory of one or more devices that are remote relative to the wearable computing device 100.

As will now be discussed, the wearable computing device 100 may be configured to process (e.g., via the machine-learned model(s) 240) optical sensor data (e.g., obtained via the optical sensor(s) 220) and movement data (e.g., obtained via the IMU 212) to identify a motion-induced spurious component of the optical sensor data. More particularly, in some examples, the wearable computing device 100 may be configured to obtain optical sensor data (e.g., via the optical sensor(s) 220) associated with the user of the wearable computing device 100. The wearable computing device 100 may also be configured to obtain movement data (e.g., via IMU 212) that characterizes a motion of the user of the wearable computing device 100. In such examples, the optical sensor data and the movement data may be provided as input(s) to the machine-learned model(s) 240, which may be configured to detect a cadence event in the optical sensor data (e.g., associated with the motion of the user). In this way, the wearable computing device 100 may identify the motion-induced spurious component of the optical sensor data based on and/or using the data (e.g., indicative of the cadence event) output by the machine-learned model(s) 240. Additionally, in some examples, the wearable computing device 100 may be operable to provide data indicative of the cadence event to the machine-learned model(s) 240 as training data for the machine-learned model(s) 240.

Figure 5:
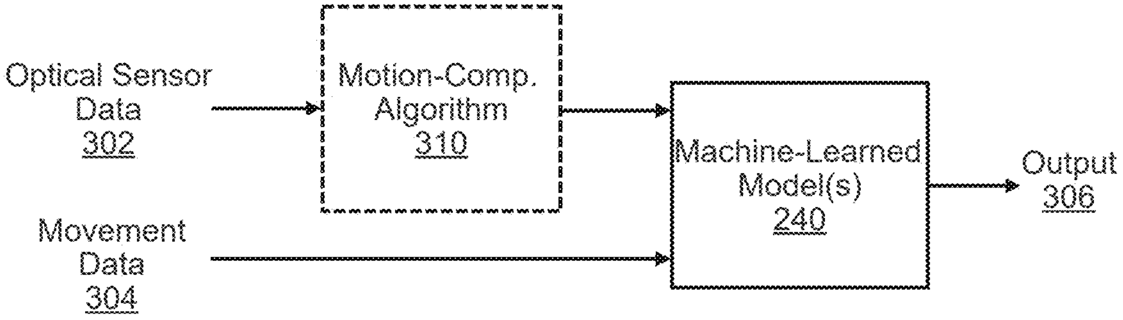
FIG. 5 depicts a block diagram of an example machine-learned model of a wearable computing device according to embodiments of the present disclosure.

Referring briefly to FIG. 5, by way of non-limiting illustrative example, a block diagram of the example machine-learned model(s) 240 is depicted according to example embodiments of the present disclosure. FIG. 5 will be discussed in conjunction with FIG. 4.

As described above, the wearable computing device 100 may obtain and/or generate optical sensor data 302 (e.g., via the optical sensor(s) 220) associated with a user of the wearable computing device 100. The wearable computing device 100 may further obtain movement data 304 (e.g., via the IMU 212) that characterizes a motion of the user of the wearable computing device 100. As noted above, in some instances, the user's motion may result in motion-induced distortions to the optical sensor data 302. Thus, the wearable computing device 100 of the present disclosure may process the optical sensor data 302 and the movement data 304 to identify a motion-induced spurious component of the optical sensor 302.

In some examples, the wearable computing device 100 may provide the optical sensor data 302 to a motion-compensation algorithm 310 to attenuate the motion-induced distortions of the optical sensor data 302. However, as noted above, a number of issues associated with the wearable computing device 100 (e.g., band attachment on the user's wrist, motion variations, wrist-size variations, etc.) may cause a pulsatile component of the optical sensor data 302 (e.g., pulsatile component of the reflected optical signal(s) received by the light detector(s) 224) to be too weak for accurate biometric parameter determinations for the user. As such, to address these issues, the wearable computing device 100 may use the movement data 304 as a reference parameter to improve the accuracy of the optical sensor data 302 and, hence, the biometric parameter determinations made for the user.

More particularly, the wearable computing device 100 may provide the optical sensor data 302 and the movement data 304 to the machine-learned model(s) 240. The machine-learned model(s) 240 may be configured to process the optical sensor data 302 and the movement data 304 to detect a cadence event (e.g., cadence lock, cadence match) that is associated with the motion of the user. In some examples, in response to detecting the cadence event in the optical sensor data 302 (e.g., via the machine-learned model(s) 240), the wearable computing device 100 may identify the motion-induced spurious component of the optical sensor data 302.

For example, to identify the motion-induced spurious component of the optical sensor data 302, the wearable computing device 100 may be configured to determine a Fast Fourier Transform (FFT) for each of the optical sensor data 302 and the movement data 304 based on the data 306 output by the machine-learned model 240. In such examples, the wearable computing device 100 may be further configured to identify the motion-induced spurious component of the optical sensor data 302 based on a relationship between the FFT for the optical sensor data 302 and the FFT for the movement data 304.

Figure 6:
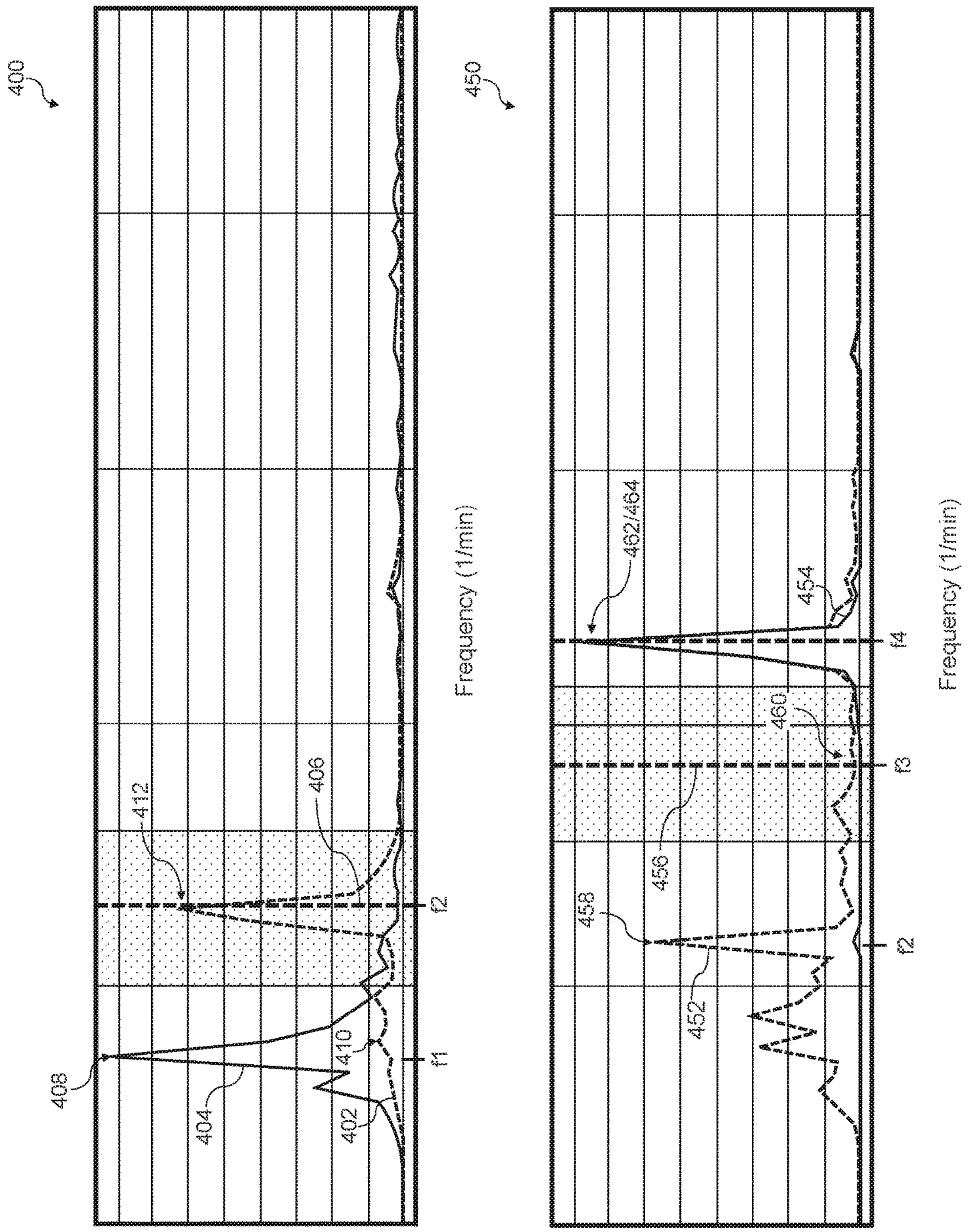
FIG. 6 depicts graphical representations of optical sensor data and movement data generated by an example wearable computing device according to embodiments of the present disclosure.

As a non-limiting illustrative example, FIG. 6 depicts graphical representations of optical sensor data and movement data generated by an example wearable computing device (e.g., wearable computing device 100) according to example embodiments of the present disclosure. More particularly, FIG. 6 depicts a graph 400 that corresponds to a situation in which no cadence event is detected by the wearable computing device 100 (FIGS. 1-5) and a graph 450 that corresponds to a situation in which a cadence lock cadence event is detected by the wearable computing device 100 (FIGS. 1-5). It should be understood that the graphs 400, 450 depicted in FIG. 6 are for purposes of illustration and discussion.

More particularly, the graph 400 depicts the frequency components of optical sensor data 402 (e.g., generated by the optical sensor(s) 220 (FIG. 4)) and the frequency components of movement data 404 (e.g., generated by the IMU 212). As described herein, the wearable computing device 100 (FIGS. 1-5) may be configured to determine a biometric parameter associated with the user based on the optical sensor data 402 and the movement data 404. Thus, for purposes of illustration and discussion, graph 400 further includes a ground-truth biometric component 406. As shown in graph 400, the movement data 404 includes a strong motion component 408 (e.g., motion peak) at frequency $f_1$. Conversely, the optical sensor data 402 includes a weak pulsatile component 410 (e.g., pulsatile peak) at frequency $f_1$. However, the optical sensor data 402 includes a strong pulsatile component 412 (e.g., pulsatile peak) at frequency $f_2$, which also corresponds to the frequency of the ground-truth biometric component 406. Hence, graph 400 depicts a situation in which no cadence event is detected by the wearable computing device 100 (FIGS. 1-5), because the optical sensor data 402 does not include a motion-induced spurious component that, if used to determine the biometric parameter associated with the user, would result in an erroneous biometric determination.

Conversely, the graph 450 depicts the frequency components of optical sensor data 452 (e.g., generated by the optical sensor(s) 220 (FIG. 4)) and the frequency components of movement data 454 (e.g., generated by the IMU 212). Furthermore, similar to the graph 400, the graph 450 further includes a ground-truth biometric component 456. As shown in graph 450, the optical sensor data 452 includes a pulsatile component 458 (e.g., pulsatile peak) at frequency $f_2$. The optical sensor data 452 further includes a weaker pulsatile component 460 at frequency $f_3$, which also corresponds to the frequency of the ground-truth biometric component 456. Furthermore, the movement data 454 includes a strong motion component 462 (e.g., motion peak) at frequency $f_4$ that also corresponds to and/or overlaps a strong motion-induced spurious component 464 of the optical sensor data 452. In such instances, if the motion-induced spurious component 464 is used (e.g., by the wearable computing device 100 (FIGS. 1-5)) to make biometric parameter determinations for the user, the resulting biometric parameter determinations would be erroneous. Hence, graph 450 depicts a situation in which a cadence lock cadence event is detected by the wearable computing device 100 (FIGS. 1-5), because the optical sensor data 452 is "locked" to the user's cadence (e.g., as indicated by the movement data 454).

Those having ordinary skill in the art, using the disclosures provided herein, will understand that the example cadence events depicted in FIG. 6 are for purposes of illustration and discussion and that the cadence events described herein are not limited to those depicted in FIG. 6.

Referring again to FIGS. 4-5, the wearable computing device 100 may be further configured to modify an operation mode of the wearable computing device 100 based on the motion-induced spurious component of the optical sensor data. More particularly, the "operation mode" of the wearable computing device 100 may correspond to a configuration of one or more of the plurality of sensors 210, such as the optical sensor(s) 220 and/or the like.

For instance, in some examples, the operation mode of the wearable computing device 100 may be modified based on a current transfer ratio (CTR) for the user. More particularly, subsequent to processing the optical sensor data and the movement data, the wearable computing device 100 may determine a signal-to-noise ratio (SNR) for the optical sensor data based on the reflected optical signal(s) received by the light detector(s) 224 of the optical sensor(s) 220. The wearable computing device 100 may further determine a signal-to-motion ratio (SMR) for the optical sensor data based on a ratio between the reflected optical signal(s) (e.g., received by the light detector(s) 224) and the movement data at a particular frequency of the optical sensor data which may, in some examples, correspond to a frequency of the motion-induced spurious component of the optical sensor data. Based on the determined CTR, the wearable computing device 100 may then determine a target signal strength for the light emitter(s) 222 of the optical sensor(s) 220 and may configure the light emitter(s) 222 to emit one or more adjusted optical signals that each have at least the target signal strength. Hence, the operation mode of the wearable computing device 100 may be modified based on the determined CTR.

In some examples, the wearable computing device 100 may be further configured to determine an acceleration profile for the user based on the movement data. As described herein, an "acceleration profile" for the user may characterize a type of physical activity being performed by the user during the sampling period in which the optical sensor data and movement data is obtained by the wearable computing device 100. In some examples, the wearable computing device 100 may further determine a correlation between the acceleration profile and the corresponding SMR. In such examples, the wearable computing device 100 may store the correlation in the memory 204 for future use. As one non-limiting example, the wearable computing device 100 may retrieve the correlation in a future situation where the user is performing the same type of physical activity and may modify the operation mode of the wearable computing device 100 based on the stored correlation.

As described herein, the wearable computing device 100 may be configured to determine a biometric parameter associated with the user, such as a heart rate (HR), based on the optical sensor data generated by optical sensor(s) 220. The wearable computing device 100 may further generate a notification for display to the user (e.g., via the output device 226) that corresponds to the biometric parameter associated with the user.

More particularly, in some examples, the wearable computing device 100 may discard the motion-induced spurious component of the optical sensor data (e.g., generated by the optical sensor(s) 220) and may identify a pulsatile component of the optical sensor data (e.g., generated by the optical sensor(s) 220) that is different from the motion-induced spurious component. In such examples, the wearable computing device 100 may determine the biometric parameter associated with the user based on the pulsatile component of the optical sensor data (e.g., generated by the optical sensor(s) 220) rather than the motion-induced spurious component, thereby increasing an accuracy of the determined biometric parameter.

Additionally and/or alternatively, subsequent to determining the biometric parameter associated with the user, the wearable computing device 100 may determine that the biometric parameter is an erroneous biometric parameter based on the motion-induced spurious component of the optical sensor data (e.g., generated by the optical sensor(s) 220). In such examples, in response to determining that biometric parameter associated with the user is the erroneous biometric parameter, the wearable computing device 100 may generate the notification (e.g., haptic notification, auditory notification, dimming the output device 226, etc.) for the user, which may indicate that the biometric parameter is the erroneous biometric parameter. Subsequently, the wearable computing device 100 may determine a corrective action for the user—which may reduce a magnitude of the motion-induced spurious component of the optical sensor data (e.g., generated by the optical sensor(s) 220)—based on the movement data (e.g., generated by the IMU 212) and the motion-induced spurious component of the optical sensor data (e.g., generated by the optical sensor(s) 220). In such examples, the wearable computing device 100 may provide a prompt to the user via the output device 226, which prompts the user to take the corrective action. By way of non-limiting example, the corrective action may be an adjustment to how and/or where the user is wearing the wearable computing device 100, an adjustment to a strap and/or band attachment that secures the wearable computing device 100 to the user, and/or the like.

As noted above, in some examples, the machine-learned model(s) 240 may be stored in the memory of one or more devices that are remote relative to the wearable computing device 100. More particularly, as shown in FIG. 4, the wearable computing device 100 may be part of the computing system 200. The computing system 200 may be used, for instance, to implement any of the methods described herein. The computing system 200 may include the wearable computing device 100, a mobile computing device 250, and a remote computing system 270. In some examples, the mobile computing device 250 may include similar components to the wearable computing device 100. For instance, in some examples, the mobile computing device 250 may include a memory (not shown) in which the machine-learned model(s) 240 is stored. In this manner, the mobile computing device 250 may be configured to perform some and/or all of the operations discussed herein with respect to the wearable computing device 100.

The wearable computing device 100 and/or the mobile computing device 250 may be communicatively coupled to the remote computing system 270 over a network 260. In some examples, the wearable computing device 100 may communicate data to the mobile computing device 250. In such examples, the wearable computing device 100 may communicate the data to the mobile computing device 250, and then the mobile computing device 250 may communicate the data over the network 260 to the remote computing system 270. Additionally and/or alternatively, in some examples, the wearable computing device 100 may bypass the mobile computing device 250 and, instead, communicate the data directly to the remote computing system 270 via the network 260.

The remote computing system 270 may include one or more processors 272. The processor(s) 272 may be any suitable processing device (e.g., a processor core, a microprocessor, an ASIC, an FPGA, a controller, a microcontroller, etc.). In some examples, the processor(s) 272 may be one processor device. Additionally and/or alternatively, in some examples, the processor(s) 272 may be a plurality of processor devices that are operatively connected.

The remote computing system 270 may further include a memory 274. The memory 274 may include one or more non-transitory computer-readable storage mediums, such as RAM, ROM, EEPROM, EPROM, flash memory devices, magnetic disks, and/or the like, and/or any combination thereof. The memory 274 may store data 276 and instructions 278 that, when executed by the processor(s) 272, cause the remote computing system 270 to perform operations, such as any of the operations described herein. In some examples, the memory 274 of the remote computing system 270 may be configured to store one or more of the machine-learned model(s) 240 described above. In this manner, the sensor data obtained from the plurality of sensors 210 onboard the wearable computing device 100 may be communicated to the remote computing system 270 and provided as an input to the machine-learned model(s) 240 stored in the memory 274 thereof.

For instance, as described herein, the machine-learned model(s) 240 may be configured to process optical sensor data (e.g., generated by the optical sensor(s) 220) and the movement data (e.g., generated by the IMU 212) and output data indicative of and/or corresponding to a motion-induced spurious component of the optical sensor data, a cadence event in the optical sensor data that is associated with a motion of the user, an acceleration profile for the user, and/or any other output described herein. In examples where the machine-learned model(s) 240 is stored in the memory 274 of the remote computing system 270 and is used to perform the operations described herein, the data output by the machine-learned model(s) 240 may be communicated over the network 260 to the wearable computing device 100.

In some examples, the remote computing system 270 may include or may otherwise be implemented by one or more computing devices (e.g., remote computing device(s), server computing device(s), etc.) (not shown). In examples where the remote computing system 270 includes plural server computing devices, such server computing devices may operate according to sequential computing architectures, parallel computing architectures, and/or any suitable combination thereof.

The network 260 may be any type of communication network, such as a local area network (LAN) (e.g., intranet), a wide-area network (WAN) (e.g., Internet), and/or any suitable combination thereof. The network 260 may include any number of wired and/or wireless communication links and/or any combination thereof. In general, communication over the network 260 may be carried by any type of wired and/or wireless connection, using any suitable communication protocol (e.g., Transmission Control Protocol/Internet Protocol (TCP/IP), Hypertext Transfer Protocol (HTTP), Simple Mail Transfer Protocol (SMTP), File Transfer Protocol (FTP), etc.), encoding or format (e.g., HyperText Markup Language (HTML), Extensible Markup Language (XML), etc.), and/or protection scheme (e.g., Virtual Private Network (VPN), secure HTTP, Secure Sockets Layer (SSL), etc.).

The technology described herein refers to sensors and other computer-based systems, as well as actions taken by, and information sent to and from, such systems. Those having ordinary skill in the art, using the disclosures provided herein, will recognize that the inherent flexibility of computer-based systems allows for a great variety of possible configurations, combinations, and/or divisions of tasks and functionality between and/or among the components thereof. As an example, server processes described herein may be implemented using a single server and/or multiple servers working in combination. Databases and/or applications may be implemented on a single system and/or distributed across multiple systems. Distributed components may operate sequentially and/or in parallel.

Figure 7:
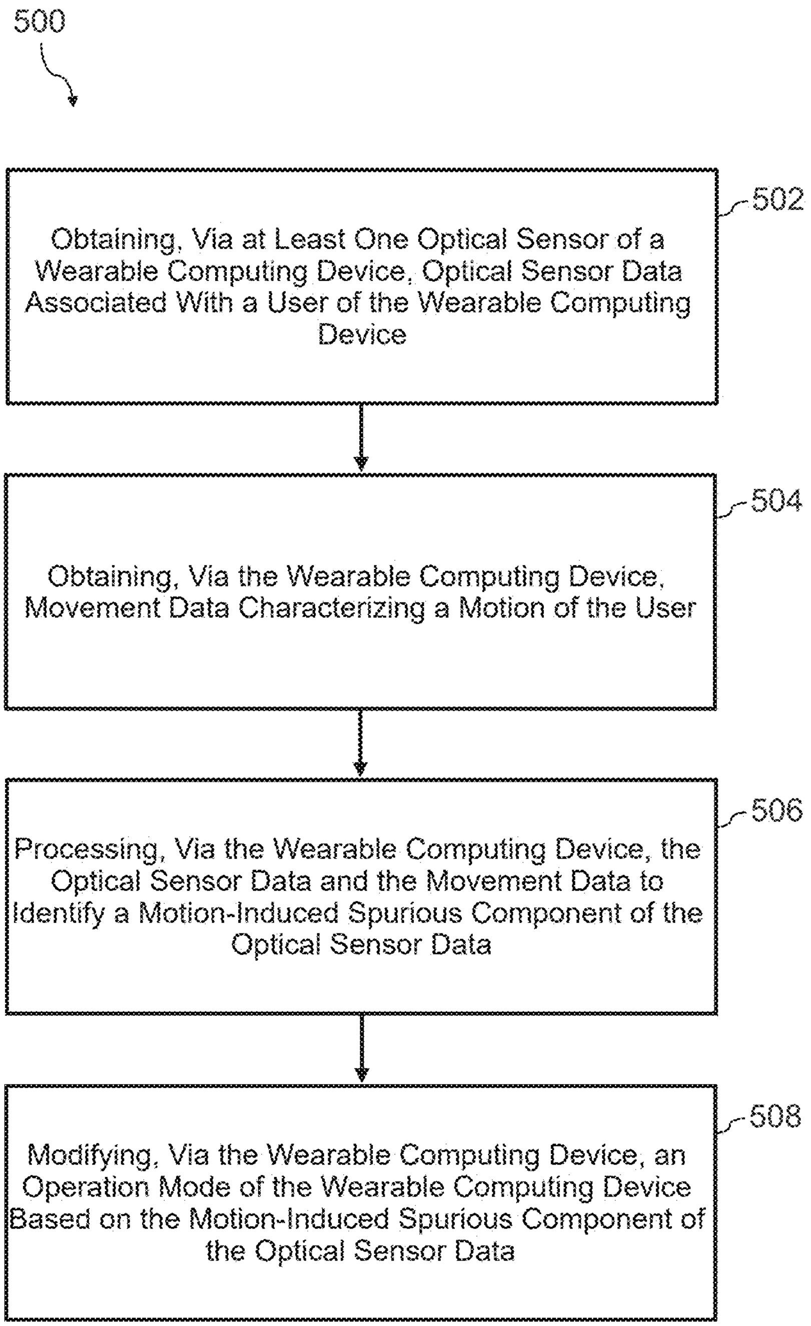
FIG. 7 depicts a flow chart diagram of an example method according to embodiments of the present disclosure.

FIG. 7 depicts a flow chart diagram of an example method 500 according to example embodiments of the present disclosure. In some examples, the method 500 may be implemented using, for instance, the wearable computing device 100 described herein. Additionally and/or alternatively, in other examples, the method 500 may be implemented by a computing device (e.g., server, smartphone, etc.) that is communicatively coupled to the wearable computing device 100. It should be understood that, in some examples, some steps of the method 500 may be implemented locally on the wearable computing device 100, whereas other steps of the method 500 may be implemented by a computing device that is remote from the wearable computing device 100 and is communicatively coupled to the wearable computing device 100 via one or more wireless networks.

FIG. 7 depicts steps performed in a particular order for purposes of illustration and discussion. Those having ordinary skill in the art, using the disclosures provided herein, will understand that various steps of any of the methods described herein may be omitted, expanded, performed simultaneously, rearranged, and/or modified in various ways without deviating from the scope of the present disclosure. Furthermore, various steps (not illustrated) may be performed without deviating from the scope of the present disclosure. Additionally, although the method 500 is generally discussed with reference to the wearable computing device 100 described herein, those having ordinary skill in the art, using the disclosures provided herein, will understand that aspects of the present method 500 may find application with any suitable computing device.

Referring now to FIG. 7 at (502), the method 500 may include obtaining, via at least one optical sensor of a wearable computing device, optical sensor data associated with a user of the wearable computing device. More particularly, as described herein, a wearable computing device (e.g., wearable computing device 100) may include an optical sensor (e.g., optical sensor 220) with one or more light emitters (e.g., light emitter(s) 222) and one or more light detectors (e.g., light detector(s) 224). In some examples, the light emitter(s) may emit one or more optical signals towards a body part of the user, and the light detector(s) may receive one or more reflected optical signals that correspond to the optical signal(s) emitted towards the body part of the user by the light emitter(s). In such examples, the wearable computing device may generate the optical sensor data based on the reflected optical signal(s) received by the light detector(s) of the optical sensor.

At (504), the method 500 may include obtaining, via the wearable computing device, movement data characterizing a motion of the user. More particularly, as described herein, the wearable computing device may include a motion sensor, such as an inertial measurement unit (IMU) (e.g., IMU 212), an accelerometer (e.g., accelerometer 214), a gyroscope (e.g., gyroscope 216), and/or the like. In some examples, the wearable computing device may generate the movement data based on sensor data from the motion sensor.

At (506), the method 500 may include processing, via the wearable computing device, the optical sensor data and the movement data to identify a motion-induced spurious component of the optical sensor data. More particularly, as described herein, the wearable computing device may provide the optical sensor data and the movement data to a machine-learned model (e.g., machine-learned model(s) 240) of the wearable computing device. In some examples, the wearable computing device may determine a Fast Fourier Transform (FFT) for each of the optical sensor data and the movement data based on an output of the machine-learned model. In such examples, the wearable computing device may identify the motion-induced spurious component of the optical sensor data based on a relationship between the FFT of the optical sensor data and the FFT of the movement data.

Additionally and/or alternatively, in some examples, the machine-learned model may detect a cadence event in the optical sensor data that is associated with the motion of the user. In response to detecting the cadence event in the optical sensor data, the wearable computing device may identify the motion-induced spurious component of the optical sensor. Furthermore, in some examples, the wearable computing device may provide data indicative of the cadence event to the machine-learned model as training data for the machine-learned model.

At (508), the method 500 may include modifying, via the wearable computing device, an operation mode of the wearable computing device based on the motion-induced spurious component of the optical sensor data. More particularly, as described herein, the wearable computing device may determine an acceleration profile for the user based on the movement data. The acceleration profile for the user may characterize a type of physical activity performed by the user (e.g., during the sampling period associated with the optical sensor data and the movement data obtained by the wearable computing device). In such examples, the wearable computing device may modify the operation mode of the wearable computing device based on the type of physical activity characterized by the acceleration profile.

For instance, in some examples, the wearable computing device may determine a current transfer ratio (CTR) for the user based on the optical sensor data. In such examples, the wearable computing device may determine a target signal strength for the optical sensor based on the CTR and may configure the light emitter(s) of the optical sensor to emit one or more adjusted light signals that each have the target signal strength.

More particularly, subsequent to processing the optical sensor data and the movement data to identify the motion-induced spurious component of the optical sensor data, the wearable computing device may determine a signal-to-noise ratio (SNR) for the optical sensor data based on the reflected optical signal(s) received by the light detector(s). The wearable computing device may further determine a signal-to-motion ratio (SMR) for the optical sensor data based on the reflected optical signal(s) received by the light detector(s) and the movement data. As described above, the SMR for the optical sensor data may be a ratio between the reflected optical signal(s) received by the light detector(s) and the movement data at a particular frequency (e.g., corresponding to a frequency of the motion-induced spurious component of the optical sensor data). In such examples, the wearable computing device may determine the CTR for the user based on the SNR for the optical sensor data and the SMR for the optical sensor data. Furthermore, in some examples, the wearable computing device may also determine and store (e.g., in memory 204) a correlation between the acceleration profile for the user and the SMR for the optical sensor data.

In some examples, the method 500 may further include determining, via the wearable computing device, a biometric parameter (e.g., heart rate (HR), etc.) associated with the user based on the optical sensor data. For instance, in some examples, the wearable computing device may discard the motion-induced spurious component of the optical sensor data and may identify a pulsatile component of the optical sensor data. In such examples, the wearable computing device may determine the biometric parameter associated with the user based on the pulsatile component of the optical sensor data. In some examples, the method 500 may further include generating, via the wearable computing device, a notification for display to the user via a display device (e.g., output device(s) 226) of the wearable computing device that corresponds to the biometric parameter associated with the user.

In some examples, subsequent to determining the biometric parameter associated with the user, the wearable computing device may determine that the biometric parameter associated with the user is an erroneous biometric parameter based on the motion-induced spurious component of the optical sensor data. In such examples, in response to determining that the biometric parameter associated with the user is the erroneous biometric parameter, the wearable computing device may generate a notification for display to the user that indicates that the biometric parameter is the erroneous biometric parameter. Subsequent to determining that the biometric parameter associated with the user is the erroneous biometric parameter, the wearable computing device may further determine a corrective action for the user based on the movement data and the motion-induced spurious component of the optical sensor data. For instance, the corrective action may reduce a magnitude of the motion-induced spurious component of the optical sensor data. In such examples, the wearable computing device may provide a prompt to the user (e.g., via output device(s) 226) that corresponds to the corrective action.

Figure 8A:
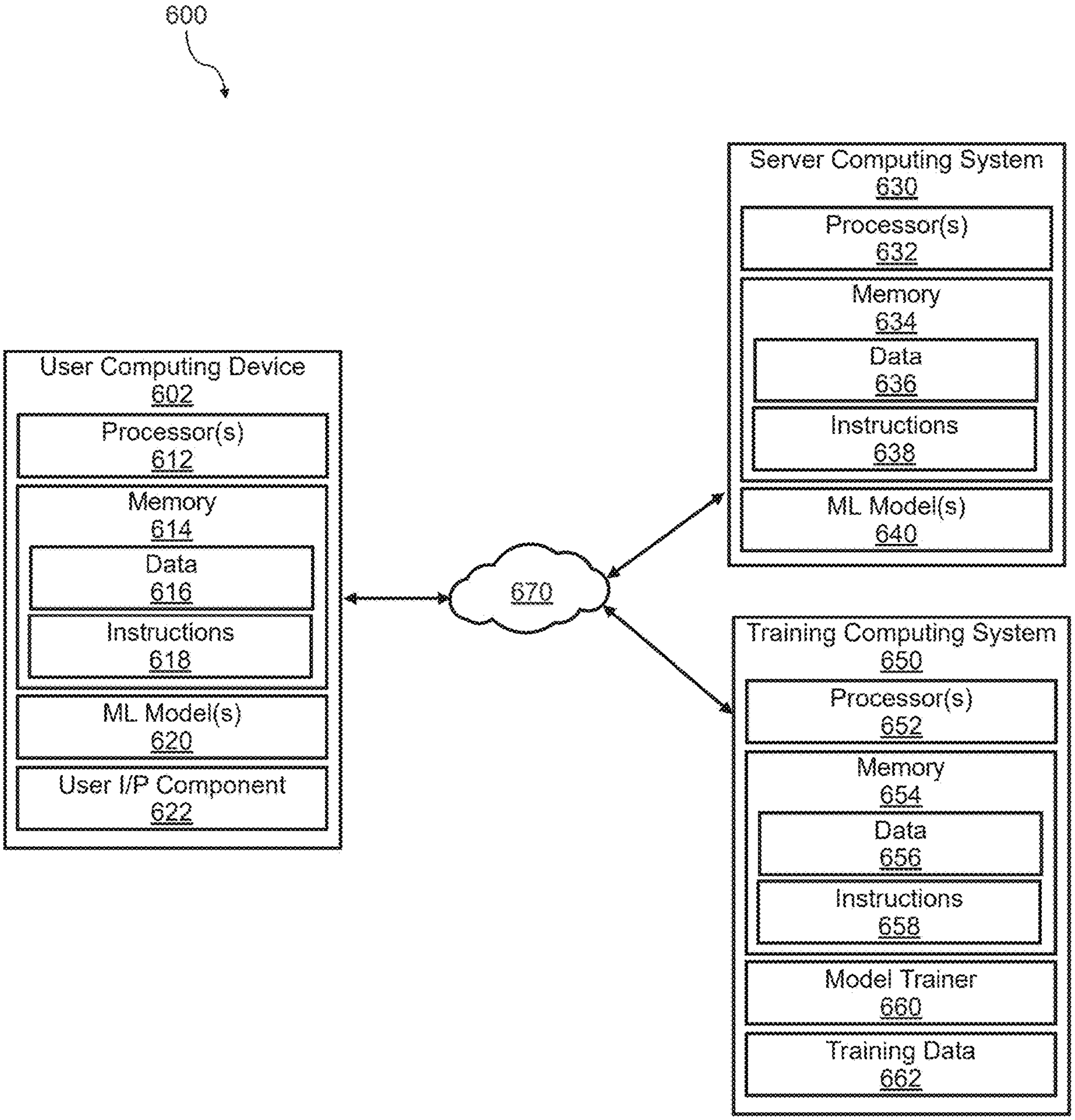
FIG. 8A depicts a block diagram of an example computing system for implementing machine-learned models according to embodiments of the present disclosure.

FIG. 8A depicts a block diagram of an example computing system 600 that performs the routing information determination operations disclosed herein according to example embodiments of the present disclosure. The system 600 includes a user computing device 602, a server computing system 630, and a training computing system 650 that are communicatively coupled over a network 670.

The user computing device 602 may be any type of computing device, such as, for example, a personal computing device (e.g., laptop or desktop), a mobile computing device (e.g., smartphone or tablet), a gaming console or controller, a wearable computing device, an embedded computing device, or any other type of computing device.

The user computing device 602 includes one or more processor device 612 and a memory 614. The one or more processor devices 612 may be any suitable processing device (e.g., a processor core, a microprocessor, an ASIC, an FPGA, a controller, a microcontroller, etc.) and may be one processor or a plurality of processors that are operatively connected. The memory 614 may include one or more non-transitory computer-readable storage media, such as RAM, ROM, EEPROM, EPROM, flash memory devices, magnetic disks, etc., and combinations thereof. The memory 614 may store data 616 and instructions 618 which are executed by the processor device 612 to cause the user computing device 602 to perform the biometric parameter determination operations, optical sensor data correction operations, etc. described herein.

In some examples, the user computing device 602 may store or include one or more machine-learned models 620. For example, the machine-learned models 620 may be or may otherwise include various machine-learned models such as neural networks (e.g., deep neural networks) or other types of machine-learned models, including non-linear models and/or linear models. Neural networks may include feed-forward neural networks, recurrent neural networks (e.g., long short-term memory recurrent neural networks), convolutional neural networks or other forms of neural networks. Some example machine-learned models may leverage an attention mechanism such as self-attention. For example, some example machine-learned models may include multi-headed self-attention models (e.g., transformer models). Example machine-learned models 620 are discussed with reference to FIGS. 1-6.

In some examples, the one or more machine-learned models 620 may be received from the server computing system 630 over network 670, stored in the user computing device memory 614, and then used or otherwise implemented by the one or more processor devices 612. In some examples, the user computing device 602 may implement multiple parallel instances of a single machine-learned model 620 (e.g., to perform the biometric parameter determination operations, optical sensor data correction operations, etc.).

More particularly, as described herein, the models may be trained to obtain and/or receive sensor data, such as optical sensor data, movement data, and/or the like. The models may be further trained to identify a motion-induced spurious component of the optical sensor data and, based on the motion-induced spurious component of the optical sensor data, modify an operation mode of the wearable computing device (not shown). In some examples, the models may be trained to determine a biometric parameter associated with a user, such as the user's heart rate (HR).

Additionally and/or alternatively, one or more machine-learned models 640 may be included in or otherwise stored and implemented by the server computing system 630 that communicates with the user computing device 602 according to a client-server relationship. For example, the machine-learned models 640 may be implemented by the server computing system 630 as a portion of a web service (e.g., an electronic record service). Thus, one or more models 620 may be stored and implemented at the user computing device 602 and/or one or more models 640 may be stored and implemented at the server computing system 630.

The user computing device 602 may also include one or more user input components 622 that receives user input. For example, the user input component 622 may be a touch-sensitive component (e.g., a touch-sensitive display screen or a touch pad) that is sensitive to the touch of a user input object (e.g., a finger or a stylus). The touch-sensitive component may serve to implement a virtual keyboard. Other example user input components include a microphone, a traditional keyboard, or other means by which a user may provide user input.

The server computing system 630 includes one or more processor devices 632 and a memory 634. The one or more processor devices 632 may be any suitable processing device (e.g., a processor core, a microprocessor, an ASIC, an FPGA, a controller, a microcontroller, etc.) and may be one processor or a plurality of processors that are operatively connected. The memory 634 may include one or more non-transitory computer-readable storage media, such as RAM, ROM, EEPROM, EPROM, flash memory devices, magnetic disks, etc., and combinations thereof. The memory 634 may store data 636 and instructions 638 which are executed by the processor device 632 to cause the server computing system 630 to perform the biometric parameter determination operations, optical sensor data correction operations, etc. described herein.

In some examples, the server computing system 630 includes or is otherwise implemented by one or more server computing devices. In instances in which the server computing system 630 includes plural server computing devices, such server computing devices may operate according to sequential computing architectures, parallel computing architectures, or some combination thereof.

As described above, the server computing system 630 may store or otherwise include one or more machine-learned models 640. For example, the models 640 may be or may otherwise include various machine-learned models. Example machine-learned models include neural networks or other multi-layer non-linear models. Example neural networks include feed forward neural networks, deep neural networks, recurrent neural networks, and convolutional neural networks. Some example machine-learned models may leverage an attention mechanism such as self-attention. For example, some example machine-learned models may include multi-headed self-attention models (e.g., transformer models). Example models 640 are discussed with reference to FIGS. 1-6.

The user computing device 602 and/or the server computing system 630 may train the models 620 and/or 640 via interaction with the training computing system 650 that is communicatively coupled over the network 670. The training computing system 650 may be separate from the server computing system 630 or may be a portion of the server computing system 630.

The training computing system 650 includes one or more processor devices 652 and a memory 654. The one or more processor devices 652 may be any suitable processing device (e.g., a processor core, a microprocessor, an ASIC, an FPGA, a controller, a microcontroller, etc.) and may be one processor or a plurality of processors that are operatively connected. The memory 654 may include one or more non-transitory computer-readable storage media, such as RAM, ROM, EEPROM, EPROM, flash memory devices, magnetic disks, etc., and combinations thereof. The memory 654 may store data 656 and instructions 658 which are executed by the processor device 652 to cause the training computing system 650 to perform the various operations described herein. In some examples, the training computing system 650 includes or is otherwise implemented by one or more server computing devices.

The training computing system 650 may include a model trainer 660 that trains the machine-learned models 620 and/or 640 stored at the user computing device 602 and/or the server computing system 630 using various training or learning techniques, such as, for example, backwards propagation of errors. For example, a loss function may be backpropagated through the model(s) to update one or more parameters of the model(s) (e.g., based on a gradient of the loss function). Various loss functions may be used such as mean squared error, likelihood loss, cross entropy loss, hinge loss, and/or various other loss functions. Gradient descent techniques may be used to iteratively update the parameters over a number of training iterations.

In some examples, performing backwards propagation of errors may include performing truncated backpropagation through time. The model trainer 660 may perform a number of generalization techniques (e.g., weight decays, dropouts, etc.) to improve the generalization capability of the models being trained.

In particular, the model trainer 660 may train the machine-learned models 620 and/or 640 based on a set of training data 662. The training data 662 may include, for example, data that is specific to a user and/or anonymized data associated with other users. The training data 662 may further include, e.g., noise to reflect expected recognition errors by the framework.

In some examples, if the user has provided consent, the training examples may be provided by the user computing device 602. Thus, in such examples, the model 620 provided to the user computing device 602 may be trained by the training computing system 650 on user-specific data received from the user computing device 602. In some instances, this process may be referred to as personalizing the model.

The model trainer 660 includes computer logic utilized to provide desired functionality. The model trainer 660 may be implemented in hardware, firmware, and/or software controlling a general-purpose processor device. For example, in some examples, the model trainer 660 includes program files stored on a storage device, loaded into a memory and executed by one or more processors. In other examples, the model trainer 660 includes one or more sets of computer-executable instructions that are stored in a tangible computer-readable storage medium such as RAM, hard disk, or optical or magnetic media.

The network 670 may be any type of communications network, such as a local area network (e.g., intranet), wide area network (e.g., Internet), or some combination thereof and may include any number of wired or wireless links. In general, communication over the network 670 may be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL).

The machine-learned models described in this specification may be used in a variety of tasks, applications, and/or use cases.

In some examples, the input to the machine-learned model(s) of the present disclosure may be image data. The machine-learned model(s) may process the image data to generate an output. As an example, the machine-learned model(s) may process the image data to generate an image recognition output (e.g., a recognition of the image data, a latent embedding of the image data, an encoded representation of the image data, a hash of the image data, etc.). As another example, the machine-learned model(s) may process the image data to generate an image segmentation output. As another example, the machine-learned model(s) may process the image data to generate an image classification output. As another example, the machine-learned model(s) may process the image data to generate an image data modification output (e.g., an alteration of the image data, etc.). As another example, the machine-learned model(s) may process the image data to generate an encoded image data output (e.g., an encoded and/or compressed representation of the image data, etc.). As another example, the machine-learned model(s) may process the image data to generate an upscaled image data output. As another example, the machine-learned model(s) may process the image data to generate a prediction output.

In some examples, the input to the machine-learned model(s) of the present disclosure may be text or natural language data. The machine-learned model(s) may process the text or natural language data to generate an output. As an example, the machine-learned model(s) may process the natural language data to generate a language encoding output. As another example, the machine-learned model(s) may process the text or natural language data to generate a latent text embedding output. As another example, the machine-learned model(s) may process the text or natural language data to generate a translation output. As another example, the machine-learned model(s) may process the text or natural language data to generate a classification output. As another example, the machine-learned model(s) may process the text or natural language data to generate a textual segmentation output. As another example, the machine-learned model(s) may process the text or natural language data to generate a semantic intent output. As another example, the machine-learned model(s) may process the text or natural language data to generate an upscaled text or natural language output (e.g., text or natural language data that is higher quality than the input text or natural language, etc.). As another example, the machine-learned model(s) may process the text or natural language data to generate a prediction output.

In some examples, the input to the machine-learned model(s) of the present disclosure may be speech data. The machine-learned model(s) may process the speech data to generate an output. As an example, the machine-learned model(s) may process the speech data to generate a speech recognition output. As another example, the machine-learned model(s) may process the speech data to generate a speech translation output. As another example, the machine-learned model(s) may process the speech data to generate a latent embedding output. As another example, the machine-learned model(s) may process the speech data to generate an encoded speech output (e.g., an encoded and/or compressed representation of the speech data, etc.). As another example, the machine-learned model(s) may process the speech data to generate an upscaled speech output (e.g., speech data that is higher quality than the input speech data, etc.). As another example, the machine-learned model(s) may process the speech data to generate a textual representation output (e.g., a textual representation of the input speech data, etc.). As another example, the machine-learned model(s) may process the speech data to generate a prediction output.

In some examples, the input to the machine-learned model(s) of the present disclosure may be latent encoding data (e.g., a latent space representation of an input, etc.). The machine-learned model(s) may process the latent encoding data to generate an output. As an example, the machine-learned model(s) may process the latent encoding data to generate a recognition output. As another example, the machine-learned model(s) may process the latent encoding data to generate a reconstruction output. As another example, the machine-learned model(s) may process the latent encoding data to generate a search output. As another example, the machine-learned model(s) may process the latent encoding data to generate a reclustering output. As another example, the machine-learned model(s) may process the latent encoding data to generate a prediction output.

In some examples, the input to the machine-learned model(s) of the present disclosure may be statistical data. Statistical data may be, represent, or otherwise include data computed and/or calculated from some other data source. The machine-learned model(s) may process the statistical data to generate an output. As an example, the machine-learned model(s) may process the statistical data to generate a recognition output. As another example, the machine-learned model(s) may process the statistical data to generate a prediction output. As another example, the machine-learned model(s) may process the statistical data to generate a classification output. As another example, the machine-learned model(s) may process the statistical data to generate a segmentation output. As another example, the machine-learned model(s) may process the statistical data to generate a visualization output. As another example, the machine-learned model(s) may process the statistical data to generate a diagnostic output.

In some examples, the input to the machine-learned model(s) of the present disclosure may be sensor data. The machine-learned model(s) may process the sensor data to generate an output. As an example, the machine-learned model(s) may process the sensor data to generate a recognition output. As another example, the machine-learned model(s) may process the sensor data to generate a prediction output. As another example, the machine-learned model(s) may process the sensor data to generate a classification output. As another example, the machine-learned model(s) may process the sensor data to generate a segmentation output. As another example, the machine-learned model(s) may process the sensor data to generate a visualization output. As another example, the machine-learned model(s) may process the sensor data to generate a diagnostic output. As another example, the machine-learned model(s) may process the sensor data to generate a detection output.

In some cases, the machine-learned model(s) may be configured to perform a task that includes encoding input data for reliable and/or efficient transmission or storage (and/or corresponding decoding). For example, the task may be an audio compression task. The input may include audio data and the output may comprise compressed audio data. In another example, the input includes visual data (e.g. one or more images or videos), the output comprises compressed visual data, and the task is a visual data compression task. In another example, the task may comprise generating an embedding for input data (e.g. input audio or visual data).

In some cases, the input includes visual data and the task is a computer vision task. In some cases, the input includes pixel data for one or more images and the task is an image processing task. For example, the image processing task may be image classification, where the output is a set of scores, each score corresponding to a different object class and representing the likelihood that the one or more images depict an object belonging to the object class. The image processing task may be object detection, where the image processing output identifies one or more regions in the one or more images and, for each region, a likelihood that region depicts an object of interest. As another example, the image processing task may be image segmentation, where the image processing output defines, for each pixel in the one or more images, a respective likelihood for each category in a predetermined set of categories. For example, the set of categories may be foreground and background. As another example, the set of categories may be object classes. As another example, the image processing task may be depth estimation, where the image processing output defines, for each pixel in the one or more images, a respective depth value. As another example, the image processing task may be motion estimation, where the network input includes multiple images, and the image processing output defines, for each pixel of one of the input images, a motion of the scene depicted at the pixel between the images in the network input.

In some cases, the input includes audio data representing a spoken utterance and the task is a speech recognition task. The output may comprise a text output which is mapped to the spoken utterance. In some cases, the task comprises encrypting or decrypting input data. In some cases, the task comprises a microprocessor performance task, such as branch prediction or memory address translation.

FIG. 8A illustrates an example computing system that may be used to implement the present disclosure. Other computing systems may be used as well. For example, in some examples, the user computing device 602 may include the model trainer 660 and the training dataset 662. In such examples, the models 620 may be both trained and used locally at the user computing device 602. In some of such examples, the user computing device 602 may implement the model trainer 660 to personalize the models 620 based on user-specific data.

Figure 8B:
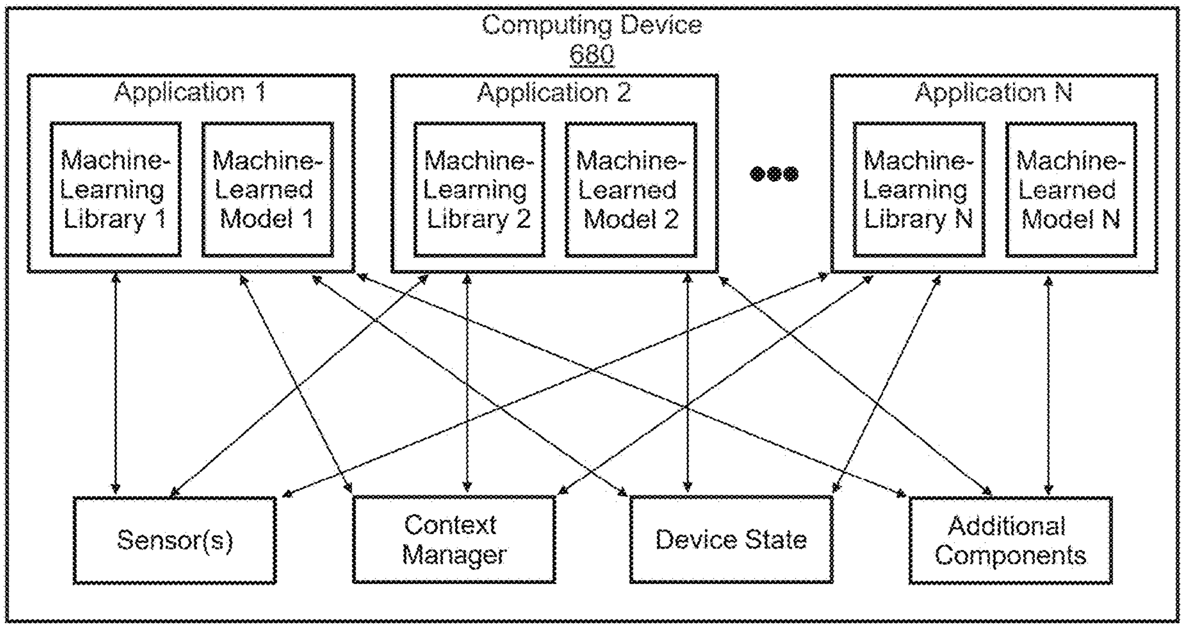
FIG. 8B depicts a block diagram of an example computing system for implementing machine-learned models according to embodiments of the present disclosure.

FIG. 8B depicts a block diagram of an example computing device 680 that performs according to example embodiments of the present disclosure. The computing device 680 may be a user computing device or a server computing device.

The computing device 680 includes a number of applications (e.g., applications 1 through N). Each application contains its own machine learning library and machine-learned model(s). For example, each application may include a machine-learned model. Example applications include a text messaging application, an email application, a dictation application, a virtual keyboard application, a browser application, etc.

As illustrated in FIG. 8B, each application may communicate with a number of other components of the computing device, such as, for example, one or more sensors, a context manager, a device state component, and/or additional components. In some examples, each application may communicate with each device component using an Application Programming Interface (API) (e.g., a public API). In some examples, the API used by each application is specific to that application.

Figure 8C:
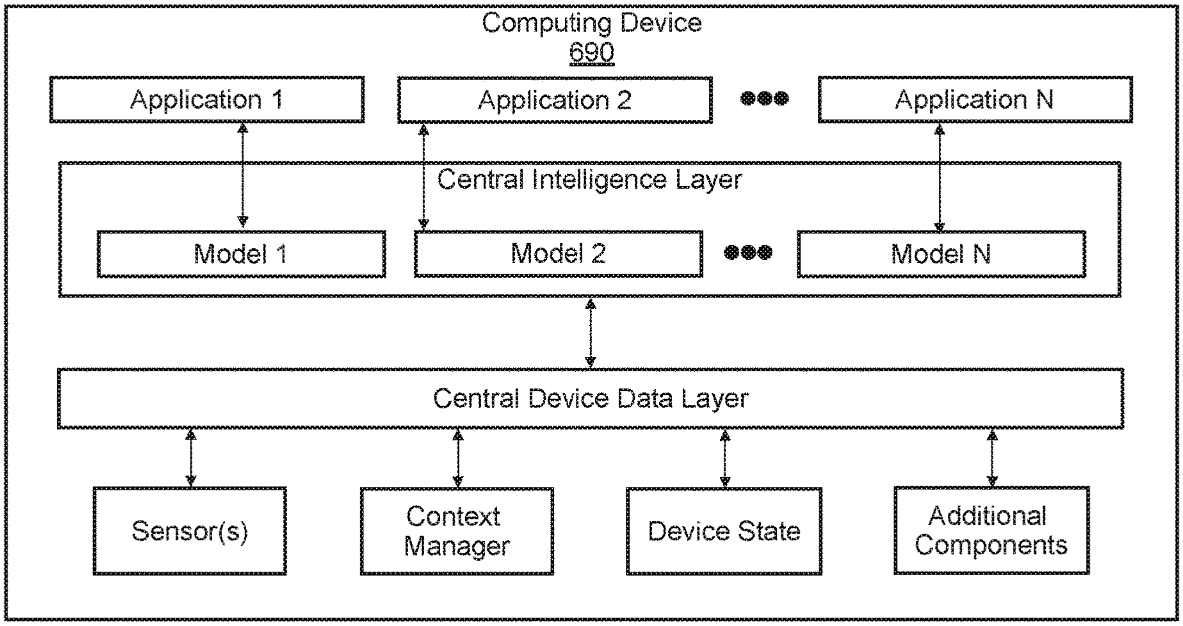
FIG. 8C depicts a block diagram of an example computing system for implementing machine-learned models according to embodiments of the present disclosure.

FIG. 8C depicts a block diagram of an example computing device 690 that performs according to example embodiments of the present disclosure. The computing device 690 may be a user computing device or a server computing device.

The computing device 690 includes a number of applications (e.g., applications 1 through N). Each application is in communication with a central intelligence layer. Example applications include a text messaging application, an email application, a dictation application, a virtual keyboard application, a browser application, etc. In some examples, each application may communicate with the central intelligence layer (and model(s) stored therein) using an API (e.g., a common API across all applications).

The central intelligence layer includes a number of machine-learned models. For example, as illustrated in FIG. 8C, a respective machine-learned model may be provided for each application and managed by the central intelligence layer. In other examples, two or more applications may share a single machine-learned model. For example, in some examples, the central intelligence layer may provide a single model for all of the applications. In some examples, the central intelligence layer is included within or otherwise implemented by an operating system of the computing device 690.

The central intelligence layer may communicate with a central device data layer. The central device data layer may be a centralized repository of data for the computing device 690. As illustrated in FIG. 8C, the central device data layer may communicate with a number of other components of the computing device, such as, for example, one or more sensors, a context manager, a device state component, and/or additional components. In some examples, the central device data layer may communicate with each device component using an API (e.g., a private API).

While the present subject matter has been described in detail with respect to specific example embodiments thereof, it will be appreciated that those skilled in the art, upon attaining an understanding of the foregoing can readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A method, comprising:

obtaining, via at least one optical sensor of a wearable computing device, optical sensor data associated with a user of the wearable computing device, the at least one optical sensor comprising one or more light emitters;

obtaining, via the wearable computing device, movement data characterizing a motion of the user;

processing, via the wearable computing device, the optical sensor data and the movement data to identify a motion-induced spurious component of the optical sensor data; and modifying, via the wearable computing device, an operation mode of the wearable computing device based on the motion-induced spurious component of the optical sensor data by:

determining, via the wearable computing device, a current transfer ratio (CTR) for the user based on a signal-to-motion ratio (SMR) for the optical sensor data, the SMR being a ratio between the optical sensor data and the movement data at a particular frequency corresponding to a frequency of the motion-induced spurious component;

determining, via the wearable computing device, a target signal strength for the at least one optical sensor based on the CTR; and configuring, via the wearable computing device, the one or more light emitters of the at least one optical sensor to emit adjusted optical signals having the target signal strength.

2. The method of claim 1, wherein processing the optical sensor data and the movement data to identify the motion-induced spurious component of the optical sensor data comprises:

providing, via the wearable computing device, the optical sensor data and the movement data to a machine-learned model of the wearable computing device;

determining, via the wearable computing device, a Fast Fourier Transform (FFT) for each of the optical sensor data and the movement data based on an output of the machine-learned model; and identifying, via the wearable computing device, the motion-induced spurious component of the optical sensor data based on a relationship between the FFT of the optical sensor data and the FFT of the movement data.

3. The method of claim 1, further comprising:

determining, via the wearable computing device, a biometric parameter associated with the user based on the optical sensor data; and generating, via the wearable computing device, a notification for display to the user via a display device of the wearable computing device, the notification corresponding to the biometric parameter associated with the user.

4. The method of claim 3, wherein the biometric parameter is a heart rate (HR) of the user.

5. The method of claim 3, wherein generating the notification for display to the user comprises:

subsequent to determining the biometric parameter associated with the user, determining, via the wearable computing device, that the biometric parameter associated with the user is an erroneous biometric parameter based on the motion-induced spurious component of the optical sensor data; and in response to determining that the biometric parameter associated with the user is the erroneous biometric parameter, generating, via the wearable computing device, the notification for display to the user, the notification indicating that the biometric parameter is the erroneous biometric parameter.

6. The method of claim 5, further comprising:

subsequent to determining that the biometric parameter associated with the user is the erroneous biometric parameter, determining, via the wearable computing device, a corrective action for the user based on the movement data and the motion-induced spurious component of the optical sensor data; and providing, via the display device of the wearable computing device, a prompt to the user, the prompt corresponding to the corrective action, wherein the corrective action reduces a magnitude of the motion-induced spurious component of the optical sensor data.

7. The method of claim 3, wherein determining the biometric parameter associated with the user comprises:

discarding, via the wearable computing device, the motion-induced spurious component of the optical sensor data;

identifying, via the wearable computing device, a pulsatile component of the optical sensor data, the pulsatile component being different from the motion-induced spurious component; and determining, via the wearable computing device, the biometric parameter associated with the user based on the pulsatile component of the optical sensor data.

8. The method of claim 1, wherein modifying the operation mode of the wearable computing device comprises:

determining, via the wearable computing device, an acceleration profile for the user based on the movement data, the acceleration profile characterizing a type of physical activity performed by the user; and modifying, via the wearable computing device, the operation mode of the wearable computing device based on the type of physical activity characterized by the acceleration profile.

9. The method of claim 1, wherein the at least one optical sensor of the wearable computing device further comprises one or more light detectors, and wherein obtaining the optical sensor data comprises:

emitting, via the one or more light emitters of the optical sensor, one or more optical signals towards a body part of the user;

receiving, via the one or more light detectors of the optical sensor, one or more reflected optical signals, the one or more reflected optical signals corresponding to the one or more optical signals emitted towards the body part of the user by the one or more light emitters; and generating, via the wearable computing device, the optical sensor data based on the one or more reflected optical signals received by the one or more light detectors of the optical sensor.

10. The method of claim 9, wherein determining the CTR for the user comprises:

subsequent to processing the optical sensor data and the movement data to identify the motion-induced spurious component of the optical sensor data, determining, via the wearable computing device, a signal-to-noise ratio (SNR) for the optical sensor data based on the one or more reflected optical signals received by the one or more light detectors;

determining, via the wearable computing device the SMR for the optical sensor data based on the one or more reflected optical signals received by the one or more light detectors and the movement data; and determining, via the wearable computing device, the CTR for the user based on the SNR for the optical sensor data and the SMR for the optical sensor data.

11. The method of claim 10, further comprising:

determining, via the wearable computing device, an acceleration profile for the user based on the movement data, the acceleration profile characterizing a type of physical activity performed by the user;

determining, via the wearable computing device, a correlation between the acceleration profile and the SMR for the optical sensor data; and storing, via the wearable computing device, the correlation in a memory of the wearable computing device.

12. The method of claim 10, wherein the SMR for the optical sensor data is a ratio between the one or more reflected optical signals received by the one or more light detectors of the optical sensor and the movement data at a particular frequency of the optical sensor data.

13. The method of claim 1, wherein processing the optical sensor data and the movement data to identify the motion-induced spurious component of the optical sensor data comprises:

providing, via the wearable computing device, the optical sensor data and the movement data to a machine-learned model of the wearable computing device;

detecting, via the machine-learned model of the wearable computing device, a cadence event in the optical sensor data that is associated with the motion of the user; and in response to detecting the cadence event in the optical sensor data, identifying, via the wearable computing device, the motion-induced spurious component of the optical sensor data.

14. The method of claim 13, further comprising:

providing, via the wearable computing device, data indicative of the cadence event to the machine-learned model as training data for the machine-learned model.

15. A wearable computing device, comprising:

a display device;

an inertial measurement unit (IMU);

one or more optical sensors comprising one or more light emitters; and one or more processors configured to:

obtain, via the one or more optical sensors, optical sensor data associated with a user of the wearable computing device;

obtain, via the IMU, movement data characterizing motion of the user;

process the optical sensor data and the movement data to identify a motion-induced spurious component of the optical sensor data; and modify an operation mode of the wearable computing device based on the motion-induced spurious component of the optical sensor data by:

determining a current transfer ratio (CTR) for the user based on a signal-to-motion ratio (SMR) for the optical sensor data, the SMR being a ratio between the optical sensor data and the movement data at a particular frequency corresponding to a frequency of the motion-induced spurious component;

determining a target signal strength for the one or more optical sensors based on the CTR; and configuring the one or more light emitters of the one or more optical sensors to emit adjusted optical signals having the target signal strength.

16. The wearable computing device of claim 15, wherein, to identify the motion-induced spurious component of the optical sensor data, the one or more processors are configured to:

provide the optical sensor data and the movement data to a machine-learned model of the wearable computing device;

determine a Fast Fourier Transform (FFT) for each of the optical sensor data and the movement data based on an output of the machine-learned model; and identify the motion-induced spurious component of the optical sensor data based on a relationship between the FFT of the optical sensor data and the FFT of the movement data.

17. The wearable computing device of claim 15, wherein the one or more processors are further configured to:

determine a biometric parameter associated with the user based on the optical sensor data; and generate a notification for display to the user via the display device, the notification corresponding to the biometric parameter associated with the user, wherein the biometric parameter associated with the user is a heart rate (HR) of the user.

18. A computing system, comprising:

an inertial measurement unit (IMU);

one or more optical sensors comprising one or more light emitters;

one or more processors; and one or more computer-readable media that collectively store instructions that, when executed by the one or more processors, cause the computing system to perform operations, the operations comprising:

obtaining, via the one or more optical sensors, optical sensor data associated with a user of the computing system;

obtaining, by the IMU, movement data characterizing motion of the user;

processing the optical sensor data and the movement data to identify a motion-induced spurious component of the optical sensor data; and modifying an operation mode of a wearable computing device of the computing system based on the motion-induced spurious component of the optical sensor data by:

determining a current transfer ratio (CTR) for the user based on a signal-to-motion ratio (SMR) for the optical sensor data, the SMR being a ratio between the optical sensor data and the movement data at a particular frequency corresponding to a frequency of the motion-induced spurious component;

determining a target signal strength for the one or more optical sensors based on the CTR; and configuring the one or more light emitters of the one or more optical sensors to emit adjusted optical signals having the target signal strength.

* * * * *